US006788018B1

(12) United States Patent
Blumenkranz

(10) Patent No.: US 6,788,018 B1
(45) Date of Patent: Sep. 7, 2004

(54) CEILING AND FLOOR MOUNTED SURGICAL ROBOT SET-UP ARMS

(75) Inventor: Stephen J. Blumenkranz, Redwood City, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 25 days.

(21) Appl. No.: 10/028,999

(22) Filed: Dec. 20, 2001

Related U.S. Application Data

(63) Continuation-in-part of application No. 09/368,309, filed on Aug. 3, 1999, now Pat. No. 6,246,200.
(60) Provisional application No. 60/258,058, filed on Dec. 22, 2000.

(51) Int. Cl.[7] .............................. G05B 19/19; B25J 5/00; B25J 11/00
(52) U.S. Cl. .............................. 318/568.11; 318/568.12; 318/568.21; 318/568.25; 901/1; 901/15; 901/30; 128/DIG. 7
(58) Field of Search ........................ 318/568.11, 568.12, 318/568.16, 568.19, 568.21, 568.25; 901/1, 2, 15, 16, 26, 30, 41, 46; 128/DIG. 7, DIG. 26, 897, 898, 899; 600/117; 601/1

(56) References Cited

U.S. PATENT DOCUMENTS

| | | |
|---|---|---|
| 5,050,608 A | 9/1991 | Watanabe et al. |
| 5,078,140 A | 1/1992 | Kwoh |
| 5,184,601 A | 2/1993 | Putman |
| 5,269,305 A | 12/1993 | Corol |
| 5,279,309 A | 1/1994 | Taylor et al. |
| 5,343,385 A | 8/1994 | Joskowics et al. |
| 5,351,676 A | 10/1994 | Putman |
| 5,378,968 A | 1/1995 | Ezawa et al. |
| 5,397,323 A | 3/1995 | Taylor et al. |
| 5,417,210 A | 5/1995 | Funda et al. |

(List continued on next page.)

FOREIGN PATENT DOCUMENTS

| | | |
|---|---|---|
| WO | WO 95/01757 | 1/1995 |
| WO | WO 99/50721 | 10/1999 |

OTHER PUBLICATIONS

Alexander Arthur D., III, "Impacts of telemation on modern society" *On Theory and Practice of Robots and Manipulators*, vol. II (1974) Springer–Verlag, New York, pp. 121–136.

*Primary Examiner*—Rina Duda
*Assistant Examiner*—Edgardo San Martin
(74) *Attorney, Agent, or Firm*—Townsend and Townsend and Crew LLP

(57) ABSTRACT

The present invention generally relates to surgical devices, systems, and methods, especially for minimally invasive surgery, and more particularly provides structures and techniques for aligning a robotic surgery system with a desired surgical site. The present invention describes techniques for mounting, configuring and arranging set-up arms for the surgical manipulators and endoscope drive mechanisms of a telesurgical system within an operating theater. The various aspects of the invention improve and optimize space utilization in the conduct of a surgical procedure, especially in the telesurgical systems which provide for concurrent operation by two surgeons using multiple robotic arm assemblies. In one aspect, the invention includes a method and apparatus for ceiling-height mounting of surgical set-up arms, and in another aspect, the invention includes a method and apparatus for the mounting of surgical setup arms to the table pedestal or floor below an operating table. The ceiling-height-mounted robotic arm assembly and below-table-mounted robotic arm assembly may be pre-configured to be ready for surgery while the fixable set-up arms are disposed generally clear of the personnel-usable space adjacent the operating table. Examples are described of separate and combined use of the ceiling mount and floor/pedestal mount aspects in both single and dual surgeon telesurgical systems.

59 Claims, 13 Drawing Sheets

U.S. PATENT DOCUMENTS

| | | |
|---|---|---|
| 5,441,042 A | 8/1995 | Putman |
| 5,441,505 A | 8/1995 | Nakamura |
| 5,445,166 A | 8/1995 | Taylor |
| 5,494,034 A | 2/1996 | Schlondorff et al. |
| 5,597,146 A | 1/1997 | Putman |
| 5,631,973 A | 5/1997 | Green |
| 5,649,956 A | 7/1997 | Jensen et al. |
| 5,696,837 A | 12/1997 | Green |
| 5,697,939 A | 12/1997 | Kubota et al. |
| 5,737,500 A | 4/1998 | Seraji et al. |
| 5,748,767 A | 5/1998 | Raab |
| 5,762,458 A | 6/1998 | Wang et al. |
| 5,784,542 A | 7/1998 | Ohm et al. |
| 5,792,135 A | 8/1998 | Madhani et al. |
| 5,800,423 A | 9/1998 | Jensen |
| 5,807,378 A | 9/1998 | Jensen et al. |
| 5,808,665 A | 9/1998 | Green |
| 5,817,084 A | 10/1998 | Jensen |
| 5,855,583 A | 1/1999 | Wang et al. |
| 5,876,325 A | 3/1999 | Mizuno et al. |

CEILING AND FLOOR MOUNTED SURGICAL ROBOT SET-UP ARMS

CROSS-REFERENCES TO RELATED APPLICATIONS

The present application claims benefit of Provisional Patent Application Ser. No. 60/258,058, filed Dec. 22, 2000. The present application is also a Continuation-In-Part of and claims the benefit of priority from U.S. patent application Ser. No. 09/368,309, filed Aug. 3, 1999, now U.S. Pat. No. 6,246,200, entitled "Manipulator Positioning Linkage For Robotic Surgery"; which was the basis for International Application No. PCT/US99/17522, filed Aug. 3, 1999, published on Feb. 17, 2000 as WO00/07503.

The present application is also related to the following commonly owned patent applications:

U.S. Ser. No. 09/433,120, filed on Nov. 3, 1999, entitled "Cooperative Minimally Invasive Telesurgical System", which was the basis for International Application No. PCT/US99/27619, filed Nov. 18, 1999 and published as WO 00/30548 on Jun. 2, 2000;

U.S. Ser. No. 09/399,457, filed Sep. 17, 1999, entitled "Cooperative Minimally Invasive Telesurgical System";

U.S. Ser. No. 09/374,643, filed Aug. 16, 1999, entitled "Cooperative Minimally Invasive Telesurgical System"; and U.S. Ser. No. 60/095,303, filed Aug. 4, 1998, entitled "Set-Up Joints For Robotic Surgery".

The complete disclosure of each of the above identified applications are incorporated herein by reference for all purposes.

BACKGROUND OF THE INVENTION

The present invention generally relates to surgical devices, systems, and methods, especially for minimally invasive surgery, and more particularly provides structures and techniques for aligning a robotic surgery system with a desired surgical site. The present invention describes techniques for mounting, configuring and arranging robotic or configurable set-up arms for the surgical manipulators and endoscope drive mechanisms of a telesurgical system within an operating theater, and methods of improving operating room space utilization in the conduct of a robotic surgical procedure.

Minimally invasive medical techniques are aimed at reducing the extraneous physiologic impact and damage to tissue in carrying out a diagnostic or surgical procedure, thereby reducing patient recovery time, discomfort, and deleterious side effects. The average length of a hospital stay for a standard surgery is significantly longer than the average length for the equivalent surgery performed in a minimally invasive surgical manner. Patient recovery times, patient discomfort, surgical side effects, and time away from work are also reduced with minimally invasive surgery.

In traditional minimally invasive surgery, such as endoscopy, surgical instruments are introduced to an internal surgical site, often through trocar sleeves or cannulas. A body cavity, such as a patient's abdomen, may be insufflated with gas to provide improved access to a surgical site, and cannula or trocar sleeves are passed through small (approximately ½ inch) incisions to provide entry ports for endoscopic surgical instruments. The surgical instruments or tools used in traditional endoscopy may have elongate handles extending out from the cannula, to permit the surgeon to perform surgical procedures by manipulating the tools from outside the body. The portion of the tool inserted into the body may include an end effector, by which tissue is manipulated. Typically minimally invasive procedures are performed under the direction of a surgical imaging system, such as by introducing an endoscope to the surgical site for viewing the surgical field. Typically the endoscope is coupled to a digital camera, to permit remote display, the surgeon then activating the surgical instruments while viewing the surgical site on a video monitor. Similar endoscopic techniques are employed in, e.g., laparoscopy; arthroscopy, retroperitoneoscopy, pelviscopy, nephroscopy, cystoscopy, cisternoscopy, sinoscopy, hysteroscopy, urethroscopy, and the like.

Minimally invasive surgical systems have been and continue to be developed to increase a surgeon's dexterity by means of robotic telesurgical systems, so that the surgeon performs the surgical procedures on the patient by manipulating master control devices to control the motion of servo-mechanically operated instruments. In contrast to the elongate handles of traditional endoscopic tools, in robotically assisted minimally invasive surgery, or telesurgery, a servomechanism is used to actuate the surgical end effectors of the instruments. This allows the surgeon to operate in a comfortable position without looking one direction (towards the monitor) while manipulating handles of surgical instruments that are oriented in another direction (for example, into the patient's abdomen). Telesurgical or robotically operated instruments also may greatly increase the range of motion and degrees of freedom achievable for end effectors at the internal surgical site.

As more fully described in U.S. Pat. No. 5,696,837, the full disclosure of which is incorporated herein by reference, a computer processor of the servomechanism can be used to maintain the alignment between hand input devices of the controller with the image of the surgical end effectors displayed on the monitor using coordinate system transformations. This allows the surgeon to operate in a natural position using anthropomorphic hand input devices and motions aligned with the image display, despite the fact that the actual surgical instruments are inserted via otherwise awkward arbitrary access positions. The endoscope may optionally provide the surgeon with a stereoscopic image to increase the surgeon's ability to sense three-dimensional information regarding the tissue and procedure. Typically the image captured by the endoscope is digitized by a camera, such as a CCD device, and processed for display to the surgeon and surgical assistants.

In robotically assisted surgery or telesurgery, a surgeon typically operates at least one master controller to control the motion of at least one surgical instrument at the surgical site. The controller will typically include one or more hand input devices or masters, by which the surgeon inputs control movements. The master controllers and surgeon's view display of the endoscope image may be separated from the patient by a significant distance, and need not be immediately adjacent the operating table. The master controller mountings and endoscope display may be integrated as a control console, referred to herein as the "surgeon's console" portion of the telesurgical system, which may be connected by signal and power cables to the servomechanisms, endoscope cameras, processors and other surgical instrumentation. The console is typically located at least far enough from the operating table to permit unobstructed work space for surgical assistants.

Each telesurgical master controller is typically coupled (e.g., via a dedicated computer processor system and connector cables) to a servo-mechanism operating a surgical instrument. The servo mechanism articulates and operates the surgical instrument, tool or end effector to carry out the surgical procedure. A plurality of master controllers may operate a plurality of instruments or end effectors (e.g., tissue graspers, needle drivers, cautery probes, and the like) based on the surgeon's inputs. These tools perform functions for the surgeon, for example, holding or driving a needle, grasping a blood vessel, or dissecting, cauterizing, or coagulating tissue. Similarly, surgeon's master inputs may control the movement and operation of an endoscope-camera driver servomechanism, permitting the surgeon to adjust the view field and optical parameters of the endoscope as the surgery proceeds. In a typical telesurgical system, the surgeon may operate at least two surgical instruments simultaneously, (e.g., corresponding to right and left hand inputs) and operate an endoscope/camera driver by additional control inputs. Note that optionally the servo-manipulators may support and operate a wide variety of surgical tools, fluid delivery or suction devices, electrical or laser instruments, diagnostic instruments, or alternative imaging modalities (such as ultrasound, fluoroscopy, and the like).

U.S. Pat. Nos. 5,184,601; 5,445,166; 5,696,837; 5,800,423; and 5,855,583 describe various devices and linkage arrangements for robotic surgical manipulators. The full disclosure of each of these patents is incorporated by reference. The servo-mechanisms, their supporting/positioning apparatus, the surgical instruments and endoscope/camera of a telesurgical system are typically mounted or portably positioned in the immediate vicinity of the operating table, and are referred to herein collectively as the "patient-side" portion of the telesurgical system.

Generally, a supporting linkage mechanism is used to position and align each surgical servo-manipulator or endoscope probe with the respective incision and cannula in the patient's body. The supporting linkage mechanism facilitates the alignment of a surgical manipulator with a desired surgical access point. Such devices will generally be referred to herein as "setup arms", it being understood that a number of quite different mechanisms may be used for this purpose. The above referenced pending PCT/US99/17522, published on Feb. 17, 2000 as WO00/07503, describes a number of aspects and examples of manipulator positioning or setup arms, and the full disclosure of this publication is incorporated by reference.

As an example of a current telesurgical system generally embodying the principles and technology of minimally invasive robotic surgery, reference is made to the da Vinci™ Surgical System, made by Intuitive Surgical, Inc. of Mountain View, Calif., the assignee of the present application.

SUMMARY OF THE INVENTION

The present invention generally provides improved methods and mechanisms for configuring and arranging a set-up arms for the surgical manipulators and endoscope drive mechanisms so as to improve and optimize space utilization in the operating room, especially in the telesurgical systems which provide for concurrent operation by two surgeons.

A typical telesurgical system may comprise at least one surgical servo-manipulator mounted to setup arm so as to be positionable adjacent to the operating table for insertion into a cannula placed in an incision in the patient's body ("patient-side surgical manipulators or "PSM"). A typical single-surgeon system includes two such PSM, operated simultaneously by the surgeon via right and left hand controller input devices, such as master handles or grips. In addition, a typical single-surgeon system includes an endoscope/camera manipulator ("ECM"), supporting an endoscope or other endoscopic image capture device, and mounted to a setup arm so as to be positionable adjacent to the operating table for insertion into cannula placed in an additional incision in the patients body.

The telesurgical setup arms, and their respective PSM or ECM, occupy significant volume and require space to have range of motion for positioning. In addition, the environment of an operating room is often crowded with competing demands for space needed for an anesthesiologist, related equipment, surgeon's assistants, life support equipment, lights, surgical tool storage, instrumentation, displays, and the like. Therefore, one object of the invention is to provide a telesurgical setup arm mounting system which improves space utilization adjacent the operating table.

It is also desired to provide a telesurgical system which permits two-surgeons to operate cooperatively in a dual telesurgical system, including, for example, a total of four PSM and two ECM units, together with their setup arms and supports. Dual surgeon telesurgical cooperative operation is particularly desired for complicated and lengthy procedures, such as multi-vessel coronary bypass graft procedures.

At the same time, it is desired to allow reasonable access to the operating table and related equipment by an anesthesiologist and surgical assistants during the course of surgery. Where two telesurgical systems and respective setup arms are mounted on a separate cart or stand structures positioned adjacent to opposite sides of the table, in addition to the presence of personnel and other surgery-related equipment, the space tends to become quite congested. Therefore, it is another object of the invention to provide a telesurgical setup arm mounting arrangement which minimizes the intrusion by the setup arms into the personnel-usable space adjacent the operating table and which minimizes the potential for "collisions" or space conflicts with other adjacent manipulators, setup arms or equipment.

In general, the term "personnel-usable space" includes space for surgery-related equipment to be positioned adjacent the operating table and space for personnel to stand and move adjacent the table for access to and viewing of the patient and surgery-related equipment. Typically, this includes volumes adjacent the sides and ends of the table from about floor level to include standing headroom. While the manipulators and end effectors of the a robotic surgical system are generally pre-configured to a position adjacent the surgical insertion site on the patient's body, it is desirable that the setup arms or fixable linkage be pre-configured to be generally clear of the "personnel and equipment usable space", i.e., to extend into this space only minimally so as to couple to the manipulator, the principal part of the setup arm or pre-configuration linkage assembly and mounting base being disposed outside of this space.

Stated in general terms, the patient-side surgical system of the invention comprises a base, a surgical end effector, a jointed linkage supporting the end effector relative to the base and a servomechanism for moving the end effector so as to manipulate tissues. Portions of the support linkage and end effector which are servo-mechanically driven in response to the surgeon's inputs will generally be referred to herein as a "manipulator," while portions of the support linkage which are typically manually positioned by assisting personnel are generally referred to as the "setup arm." It should be noted, however, that setup arm joints and links may optionally be powered and moved under computer or operator control during the course of surgery (and before or after surgery), e.g., to optimize manipulator range of motion, to avoid "collisions" or conflicts between neighboring manipulators, to avoid mechanical singularities, to reduce setup time, to ease storage, and the like.

The exemplary embodiments of the setup arms of the invention are manually positionable or pre-configurable to allow the operator to translate the surgical manipulator and instrument in three dimensions, and to orient the surgical instrument by rotating the manipulator and instrument about one, two or three axes of rotation. The linkages preferably include lockable joints to maintain a fixed configuration and/or position until a brake system is released. While the brake is held in a released mode, the released linkage permits the operating room personnel to manually move the linkage into alignment with the surgical site. The brake system may fix the configuration of these linkages whenever the operator lets go, thereby avoiding inadvertent movement of the surgical instruments.

The linkage and joints of the setup arm system may include position tracking sensors or encoders to permit measurement of motion, position and angles of linkage elements and joints. In the case of manually positionable or pre-configurable (passive) joints, it is preferable that the joint sensors have signals vary with an absolute position of the joint, rather than solely incremental changes in position, to avoid accumulation of possible small position errors. The driven robotic joints may likewise have absolute position, motion or angle sensors. This sensor data may in turn be used for the automatic calculation of the position and alignment of the set arm and manipulators with respect to a selected coordinate system (such as for vision and display alignment), with respect to the range of motion of the setup arm element, with respect to an end effector pivot point, and with respect to neighboring setup arms and manipulators of a multi-arm telesurgical system.

Ceiling Mounted Setup Arm

In one embodiment of the invention, the setup arms articulate from base structures mounted in the ceiling of the operating room, the base structure and much of the setup arm structure being above typical head height, allowing surgical assistant access to the patient and for surgical tool changing with both tables sides unobstructed Furthermore, the setup arms may have a range of motion permitting access to cannula ports over a wide range of the patients body, without modification of the mounting. For example, the ceiling mounted arms may be moved to access both thoracic and abdominal ports. In addition, the ceiling mounting permits the setup arms and manipulators to be retracted out of the way of personnel when not in use. Cabling and power connections may be in the ceiling space, simplifying cable routing. In addition, the ceiling mounting of the setup arms reduces the extent of sterile draping required.

Although multiple setup arms may be mounted to a single ceiling base, where multiple setup arms and manipulators are ceiling mounted (e.g., for cooperative dual surgery), the respective bases may be distributed over the ceiling area to optimize manipulator access to the patient, to avoid conflict with adjacent manipulators, while minimizing conflicts with equipment or personnel located adjacent to floor or table level. The requirements for other ceiling mounted-equipment, such as lights, utility arms, display supports and the like, are considered when selecting ceiling base locations.

In one embodiment, the ceiling mounted setup arm comprises at least one parallelogram-link structure, which is force balanced in the vertical plane by one or more gas-springs. Each parallelogram may be raised and lowered vertically, with minimal residual force, the gas springs being selected to support the majority of the system weight throughout the range of motion. The parallelogram is mounted to a pivot support, providing for rotation in the horizontal plane. Preferably, there are two balanced parallelogram structures in sequence, the distal parallelogram being pivotally jointed to the proximal parallelogram, to permit an additional degree of freedom in the horizontal plane.

Balancing in the vertical plane may be provided by a conventional gas spring of selected dimensions, spring characteristics and mounting points, so as to providing light positioning action, and good force and inertia matching in X, Y, and Z directions. The balance characteristics may be selected to be near-neutral throughout the range of motion, or may be bi-stable, so as to have a predetermined raised and lowered stability points. Optionally, the parallelogram structures may be balanced by counterweights, tension springs, torsion springs, compression springs, air or hydraulic cylinders, torque motors, or combinations of these devices. Alternatively, one or more jointed SCARA-style links may be included, such as are described in the above referenced WO00/07503.

Both parallelogram structures and the pivotal mounting may be lockable, to prevent inadvertent movement once the manipulator is in the selected alignment and position. In addition, one or both parallelogram structures may be powered to assist retraction or deployment. The manipulator (PSM or ECM) maybe mounted to the distal end of the setup arm with additional degrees of freedom for patient side positioning and to avoid "collisions" or space conflicts with adjacent equipment, such as by a gimbaled or multi-stop mounting. Exemplary mountings of manipulators to setup arms are described in the above referenced WO00/07503.

Floor or Pedestal Mounted Setup Arm

In another aspect of the invention, the setup arm may be mounted to a base support on the floor adjacent to the operating table pedestal or floor adjacent to the table. The mounting is positioned to leave unobstructed floor standing or passage space on each side of the table.

The floor mounted setup arm may have a proximal link comprising a jointed SCARA link providing motion in the horizontal plane. The distal link may be a parallelogram structure similar the that of the ceiling mounted setup arm embodiment, with the gas spring mounted to provide an upward balancing force. As in the ceiling mounted setup arm, the manipulator (PSM or ECM) maybe mounted to the distal end of the setup arm with additional degrees of freedom for patient side positioning and to avoid "collisions" or space conflicts with adjacent equipment, such as by a gimbaled or multi-stop mounting. The setup arm base support is optionally positioned to permit the arms and manipulators to be stowed under the table structure when not in use.

Combined Ceiling Mounted And Floor Mounted Setup Arm System

In a preferred embodiment of a telesurgical system employing the setup arms of the invention, both floor mounted and ceiling mounted setup arms are included in combination. For example, a dual-surgeon telesurgical system may comprise a total of four ceiling mounted setup arms mounted on opposite sides of the table, and supporting four PSM units. Two floor or pedestal mounted setup arms are included, mounting two ECM units. The combination of ceiling and floor mounted setup arms makes optimal use of available table-side space while permitting the manipulators to be positioned for effective cooperative surgery by two surgeons.

These and other aspects of the invention will be further evident from the attached drawings and description of the embodiments of the invention.

DESCRIPTION OF THE SPECIFIC EMBODIMENTS

The following detailed description illustrates the invention by way of example, not by way of limitation of the principles of the invention. All publications and patent applications cited in this specification are herein incorporated by reference as if each individual publication or patent application were specifically and individually indicated to be incorporated by reference and the full disclosure of each was set forth herein.

Figure 1:
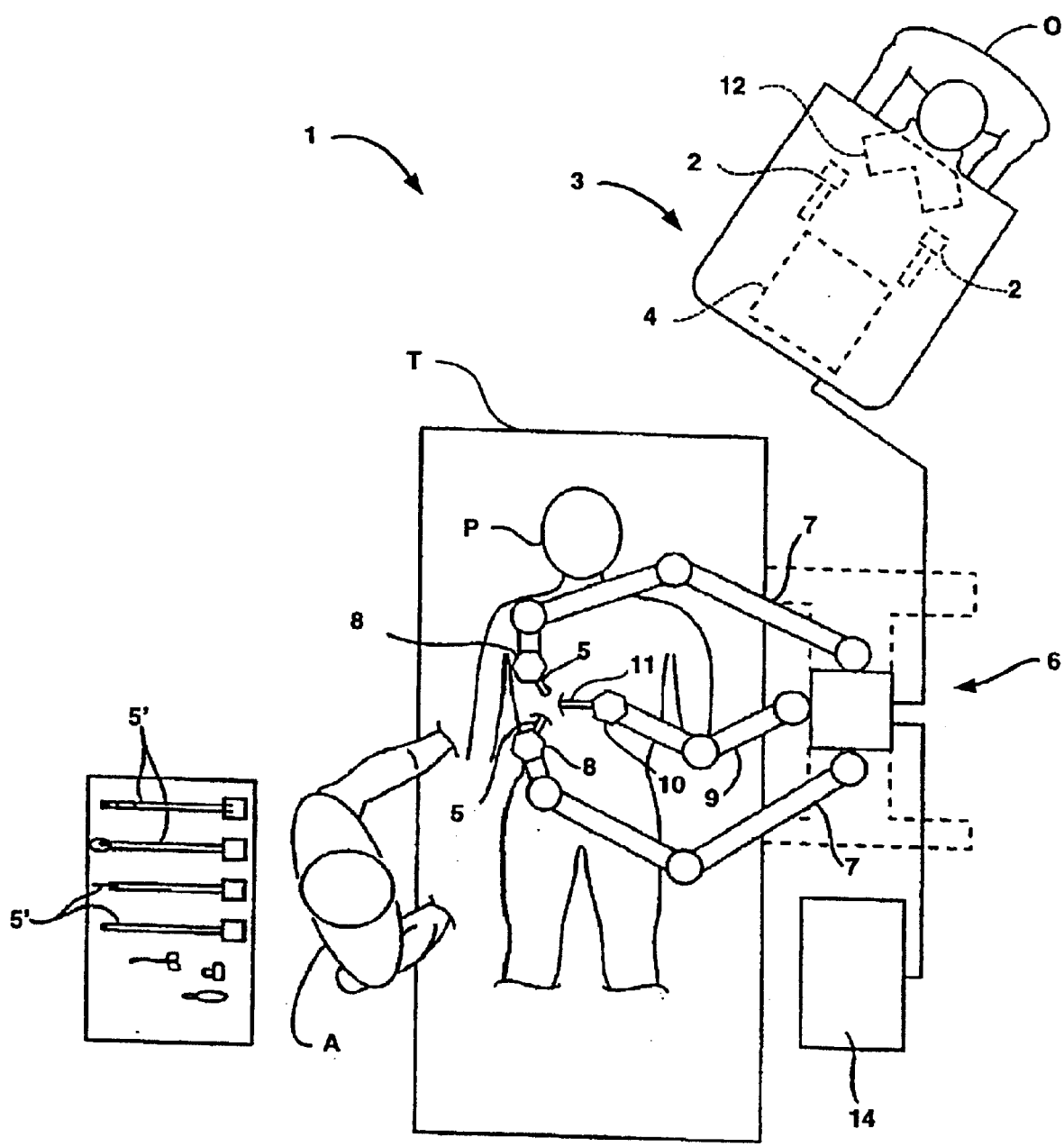
FIG. 1 is a schematic plane view of a portion of an operating room showing a robotic surgical system performing a minimally invasive robotic surgical procedure as described in WO00/07503.

FIG. 1 is a schematic plane view of a portion of an operating room showing by way of background an exemplary robotic surgical system 1 performing a minimally invasive robotic surgical procedure, such as described in WO00/7503. An operator O (generally a surgeon) performs a minimally invasive surgical procedure on patient P lying on operating table T, the operator O manipulating one or more input devices or masters 2 at a surgeon's console 3. In response to the surgeon's inputs, a computer processor 4 of console 3 directs movement of endoscopic surgical instruments or tools 5, effecting servo-mechanical movement of the instruments via a robotic patient-side system 6 (a cart-mounted system in this example).

Typically, patient side system or cart 6 includes at least three robotic manipulator arms. Two arms or linkages 7 (mounted at the sides of cart 6 in this example) support and position servo-manipulators 8 which drive surgical tools 5; and one arm or linkage 9 (mounted at the center of cart 6 in this example) supports and positions servo-manipulator 10 which controls the motion of an endoscope/camera probe 11, which captures an image (preferably stereoscopic) of the internal surgical site.

The image of the internal surgical site shown to surgeon or operator O by a stereoscopic display viewer 12 in surgeon's console 3, and is simultaneously shown to assistant A by an assistant's display 14. Assistant A assists in pre-positioning the manipulator 8 and 10 relative to patient P using setup linkage arms 7, 9, in swapping tools 5 in one or more of surgical manipulator 8 (and/or 10) for alternative surgical tools or instruments 5', in operating related non-robotic medical instruments and equipment, and the like.

In general terms, the arms or linkages 7, 9 comprise a positioning linkage or set-up arm portion of patient-side system 6, typically remaining in a fixed configuration while tissue is manipulated, and the manipulators 8, 10 comprise a driven portion which is actively articulated under the direction of surgeon's console 3. The actively driven portion is herein generally referred to as a "manipulator", and the fixable portion of the positioning linkage of patient-side system linkage is referred to herein as a "set-up arm", it being noted that such setup arms may optionally have powered and computer controlled joints as described herein.

For convenience in terminology, a manipulator such as 8 actuating tissue affecting surgical tools is generally referred to herein as a PSM (patient-side manipulator), and a manipulator such as 10 controlling an image capture or data acquisition device, such as endoscope 11, is generally referred to herein as a ECM (endoscope-camera manipulator), it being noted that such telesurgical robotic manipulators may optionally actuate, maneuver and control a wide variety of instruments, tools and devices useful in surgery.

Figure 2:
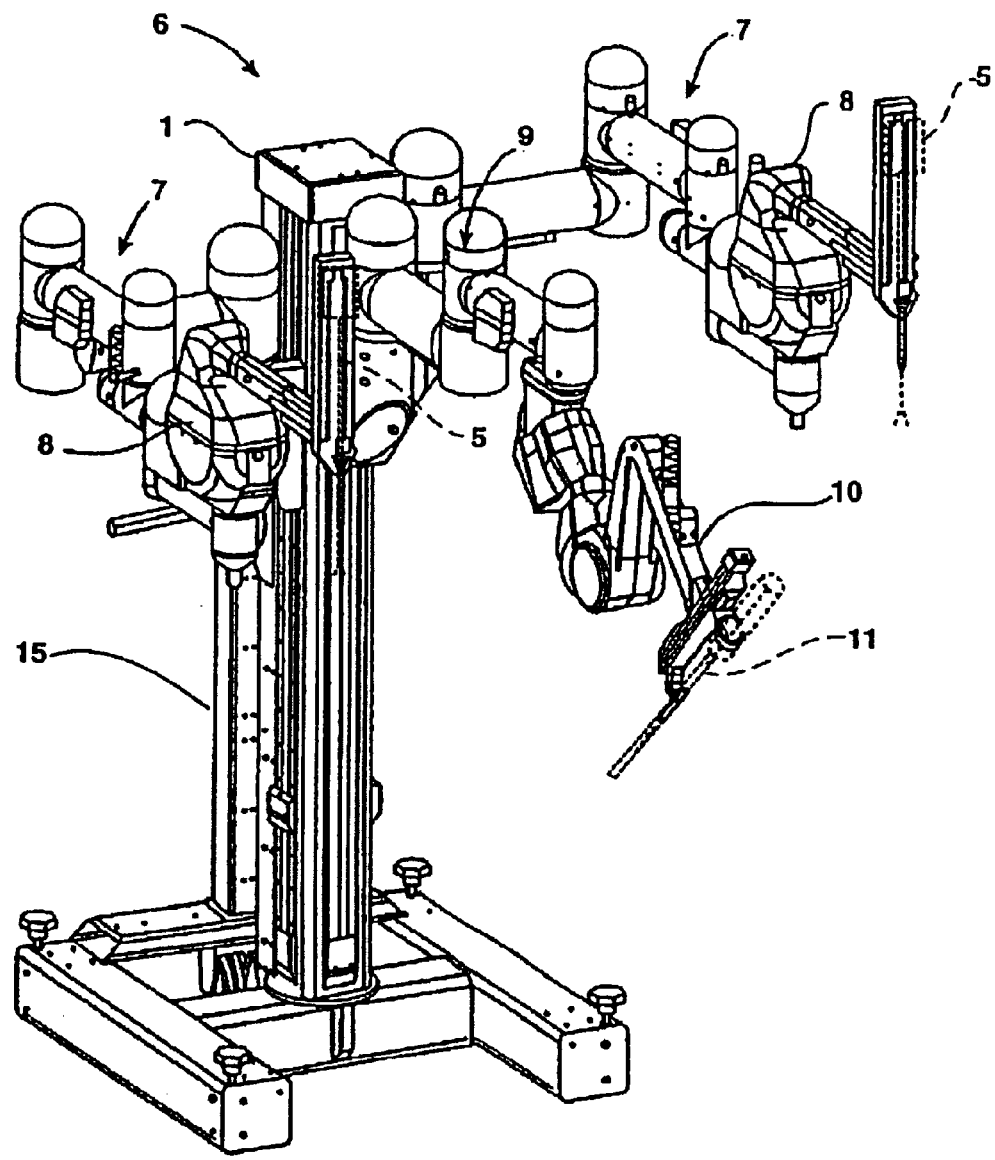
FIG. 2 illustrates a cart or stand mounted telesurgical patient-side system as described in WO00/07503, including two PSMs and one ECM.

FIG. 2 illustrates an exemplary cart mounted telesurgical patient-side system 6, such as described in WO00/7503, including two PSM 8 and one ECM 10. Cart system 6 includes a column 15 which in turn mounts three positioning linkages or setup arms, including two PSM setup arms 7, each supporting one of the PSM 8, and one ECM setup arm 9 supporting ECM 10. The PSM setup arms 7 each have six degrees of freedom, and are mounted one on each side of centrally mounted ECM setup arm 9. The ECM setup arm 9 shown has less than six degrees of freedom, and ECM 10 may not include all of the tool actuation drive system provided for articulated surgical instruments, such as are typically included in PSM 8. Each PSM 8 releasably mounts surgical tool 5 (shown in dashed lines) and ECM 10 releasably mounts endoscope probe 11(shown in dashed lines).

Figure 3B:
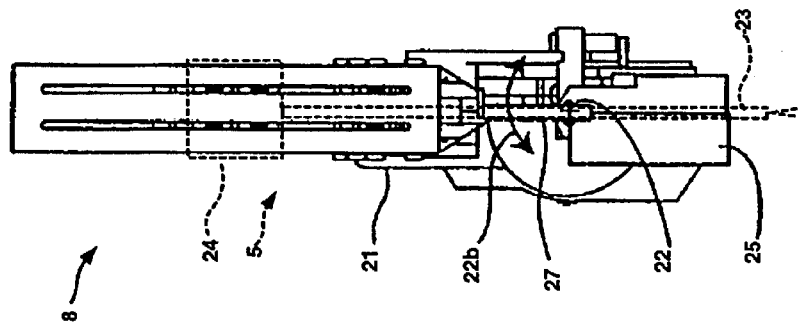
FIGS. 3A and 3B are a side and front elevation view respectively of one embodiment of a surgical robotic manipulator as described in WO00/7503.
Figure 3A:
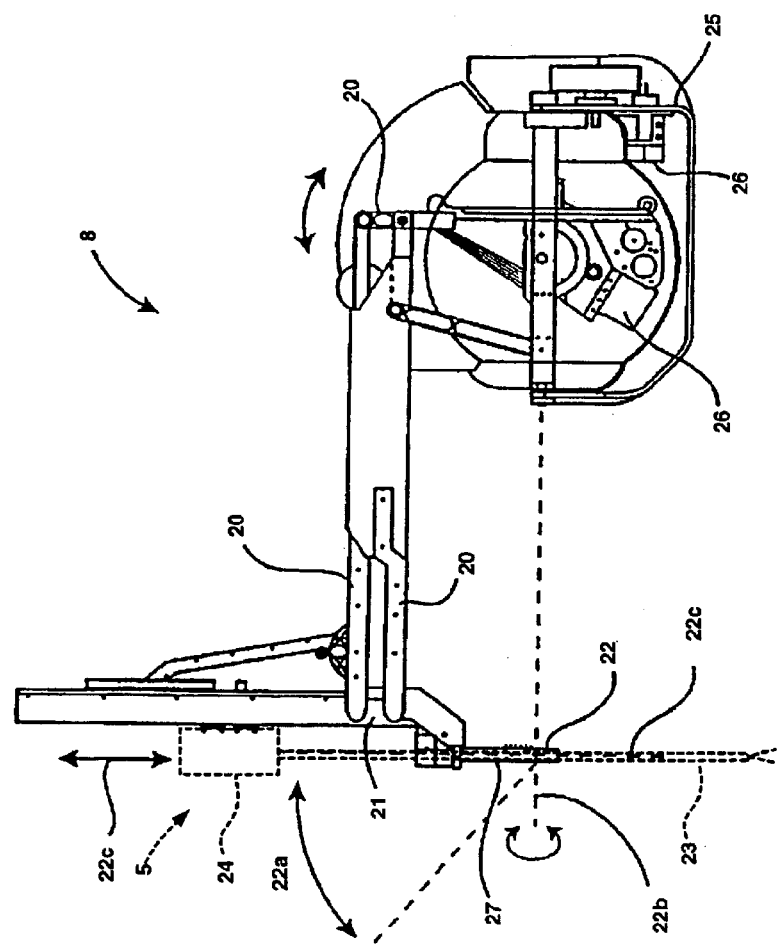

FIGS. 3A and 3B are a side and front elevation view respectively of one embodiment of a surgical manipulator or PSM 8 having a remote-center mechanism, such as described in WO00/7503. PSM 8 is but one example of a manipulator which may be mounted and supported by the ceiling mounted and floor/pedestal mounted setup arm embodiments of the current invention. In this example, the PSM 8 preferably includes a linkage arrangement 20 that constrains movement of tool interface housing 21 and mounted instrument or tool 5. More specifically, linkage 20 includes rigid links coupled together by joints in a parallelogram arrangement so that housing 21 and tool 5 rotates around a point in space 22, as more fully described in issued U.S. Pat. No. 5,817,084, the full disclosure of which is incorporated herein by reference.

The parallelogram arrangement of linkage 20 constrains rotation to pivoting, as indicated by Arrow 22a in FIG. 3A, about an axis, sometimes called the pitch axis, which is perpendicular to the page in that illustration and which passes through pivot point 22. The links supporting the parallelogram linkage are pivotally mounted to set-up joints (7 in FIG. 2) so that tool 5 further rotates about an axis 22b (FIG. 3B), sometimes called the yaw axis. The pitch and yaw axes intersect at the remote center 22, which is aligned along a shaft 23 of tool 5. Tool 5 has still further driven degrees of freedom as supported by manipulator 8, including sliding motion of the tool along insertion axis 22c. Tool 5 includes proximal housing 24 which mounts to manipulator interface housing 21. Interface housing 21 both provides for motion of the tool 5 along axis 22c and serves to transfer actuator inputs to tool 5 from the end effector actuator servo-mechanisms of PSM 8.

As tool 5 slides along axis 22c relative to manipulator 8, remote center 22 remains fixed relative to mounting base 25 (mounting point to setup arm 7) of manipulator 8. Hence, the entire manipulator is generally moved to re-position remote center 22. Linkage 20 of manipulator 8 is driven by a series of motors 26 (FIG. 3A). These motors actively move linkage 20 in response to commands from a processor (4 in FIG. 1). Motors 26 are further coupled to tool 5 so as to rotate the tool about axis 22c, and may articulate a wrist (29 in FIG. 4) at the distal end of the tool 5 about at least one, and often two, degrees of freedom. Additionally, motors 26 can be used to actuate an articulatable end effector of the tool for grasping tissues in the jaws of a forceps or the like. Motors 26 may be coupled to at least some of the joints of tool 5 using cables, as more fully described in U.S. Pat. No. 5,792,135, the full disclosure of which is also incorporated herein by reference. As described in that reference, the manipulator will often include flexible members for transferring motion from the drive components to the surgical tool. For endoscopic procedures, manipulator 8 will often include a cannula 27. Cannula 27, which may be releasably coupled to manipulator 8, supports tool 5, preferably allowing the tool to rotate and move axially through the central bore of the cannula 27.

Note that various principles of tool motion constraint may be employed by robotic surgical systems including embodiments of setup arms of the invention, in addition to the remote-center of type manipulator linkage illustrated in FIGS. 3A and 3B. In this example of a remote-center system, the parallelogram arrangement 20 is coupled to tool 5 so as to mechanically constrain the tool shaft 23 to rotation about pivot point 22 as the servomechanism actuates tool motion according to the surgeon's control inputs. Alternatively, a computed-center principle may be employed, e.g., in which the servomechanism (via its computer) calculates a shaft movement and servo action sufficient to maintain the pivot point constraint while carrying out the effects associated with the surgeon's control inputs, and servomechanically actuates the shaft accordingly. In addition the rigidity of the patients body wall may be employed to constrain the shaft (natural center), or combinations of these principles.

Figure 4:
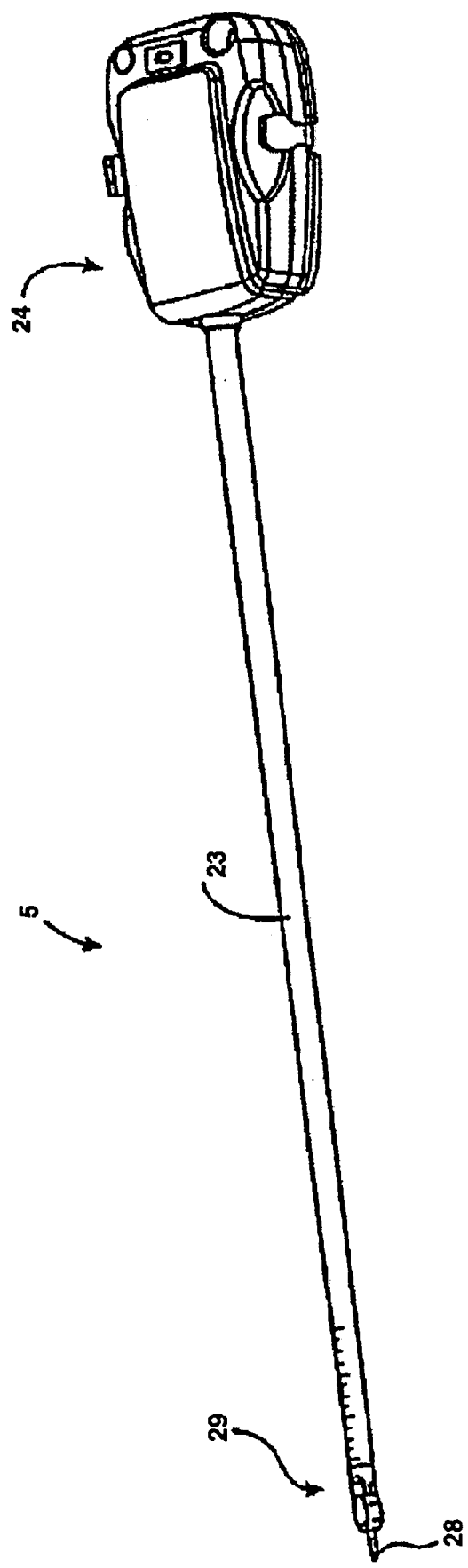
FIG. 4 illustrates an exemplary articulated surgical tool and proximal housing as described in WO00/7503.

FIG. 4 illustrates an exemplary articulated surgical tool or instrument 5 and proximal housing 24, such as described in WO00/07503. Tool 5 includes an elongate shaft 23 supporting an end effector 28 relative to a proximal housing 24. Proximal housing 24 is adapted for releasably mounting and interfacing instrument 5 to a manipulator (e.g., PSM 8 in FIGS. 1, 2, 3A, and 3B), and for transmitting drive signals and/or motion between the manipulator and end effector 28. An articulated wrist mechanism 29 may provide two degrees of freedom of motion between end effector 28 and shaft 23, and the shaft 23 may be rotatable relative to proximal housing 24 so as to provide the end effector 28 with three substantially orientational degrees of freedom within the patient's body.

Figure 5:
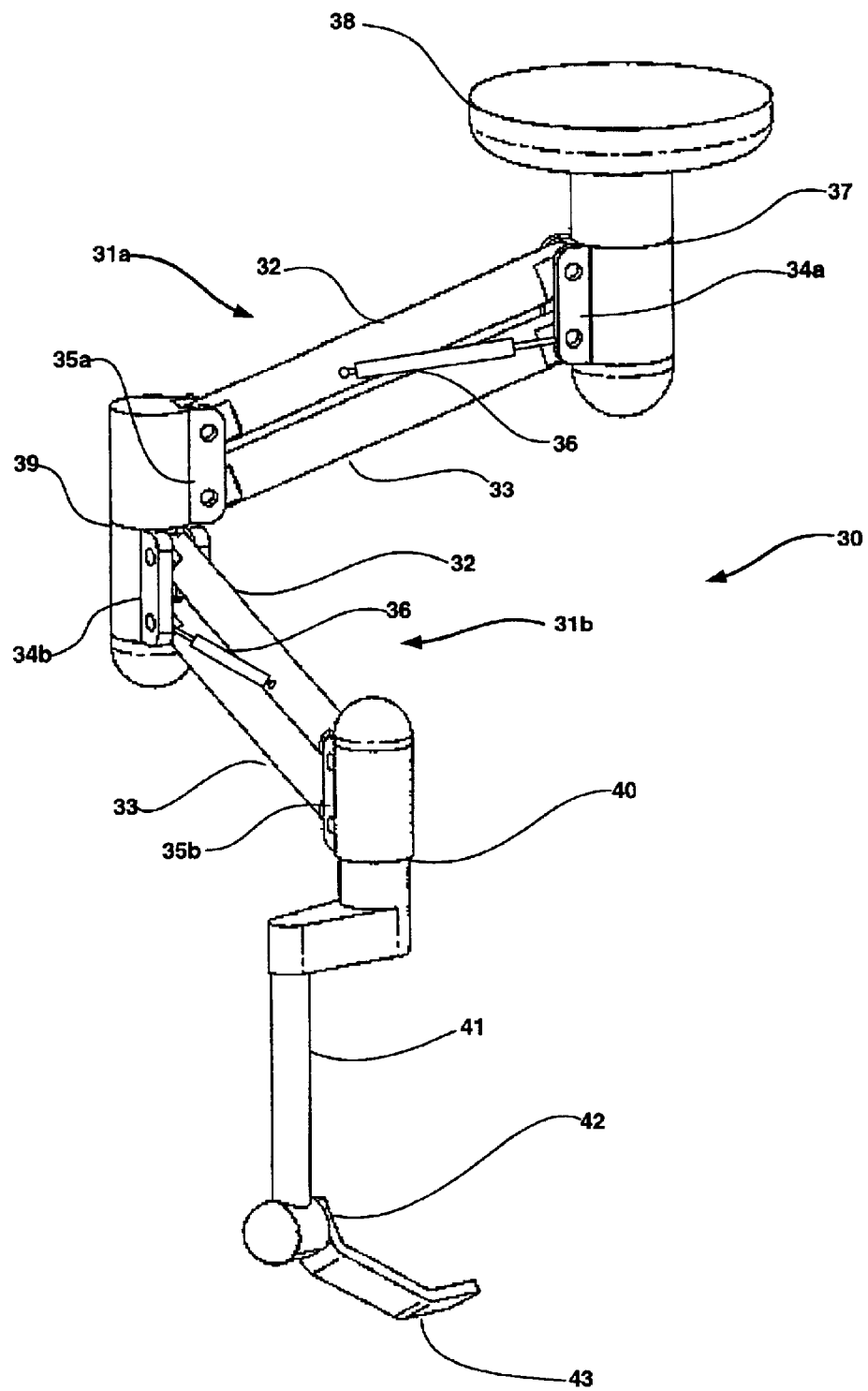
FIGS. 5 and 6 are perspective views of the linkage structure of two exemplary embodiments the ceiling mounted setup arm having aspects of the invention.
Figure 6:
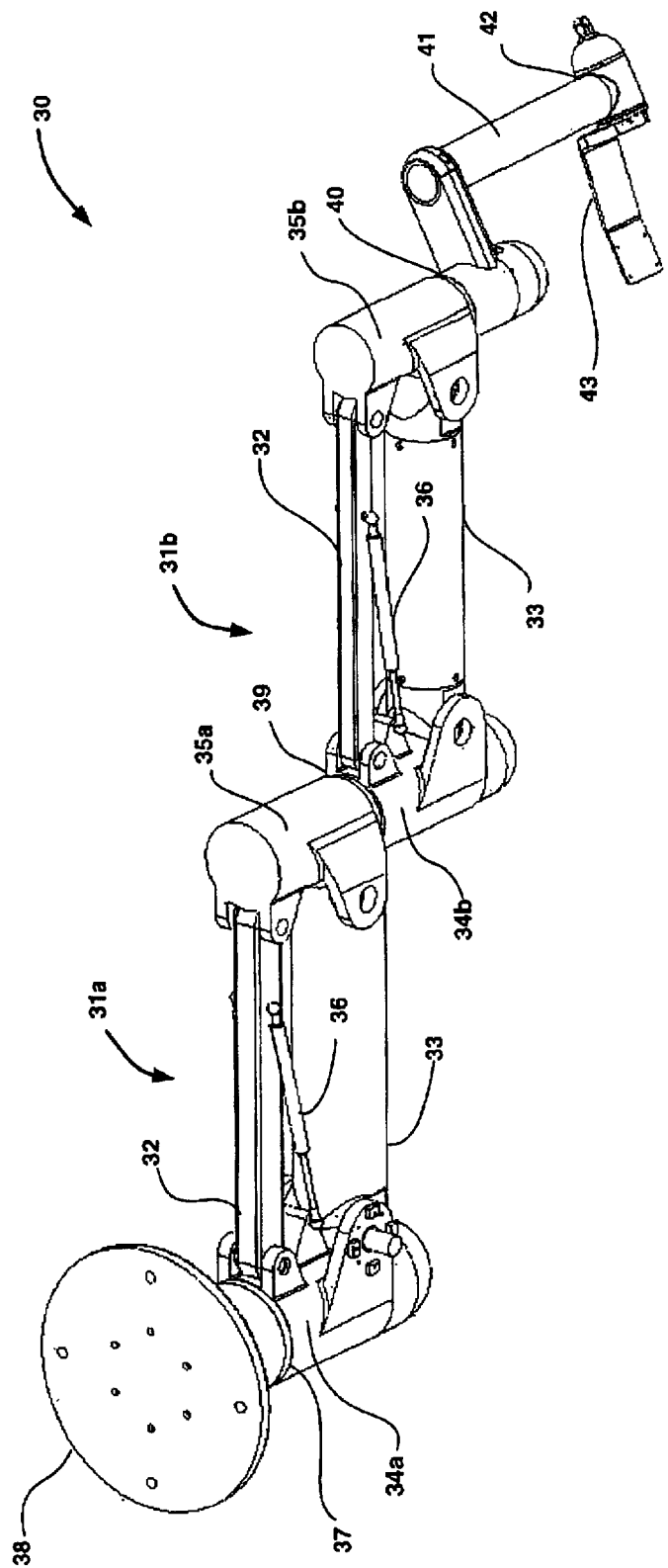

FIGS. 5 and 6 are perspective views of the linkage structure of exemplary embodiment 30 of a ceiling mounted setup arm having aspects of the invention. The setup arm 30 includes an assembly having releasably fixable joints to permit the arm 30 to be preconfigured to extend generally downward from ceiling height to support the manipulator and end effector adjacent the patient lying on the operating table. The ceiling mounted setup arm 30 comprises a pivotally connected pair of jointed-parallelogram linkage structures including upper and lower parallelogram linkage structures 31a and 31b respectively, the upper parallelogram 31a being pivotally mounted to the ceiling-height support structure (not shown).

Each of parallelogram linkage structures 31a and 31b may have a generally similar structure, in this example comprising an upper link 32, a lower link 33, a proximal bracket 34a and a distal bracket 35a. The upper and lower links 32, 33 are each pivotally jointed to proximal and distal brackets 34a, 35a respectively in a vertically-oriented planar parallelogram configuration which permits rotational motion of the links 32, 33 in the vertical plane, while constraining the brackets 34, 35 to remain substantially parallel to one another as the parallelogram 31a or 31b deforms by joint rotation.

The vertical motion of each of the linkages 31a, 31b are balanced by one or more balance mechanisms 36, such as the diagonally mounted gas springs shown in this example. In the case of the gas springs 36 shown, the spring strength, size and mounting points are selected to balance the cumulative applied vertical loads on the respective parallelogram linkages. The balance strength may be fixed at a selected mean value, or may be made adjustable, such as by adjustment screw mountings and the like. The balancing mechanism 36 may be selected (e.g., by choice of spring strength, mounting points, range spring of motion, and the like) to provide near-neutral weight balance to the setup arm 30 through its range of operative motion. Alternatively, either or both of upper and lower parallelograms 31a or 31b may be selected to favor a bi-stable preference for first fully raised position (to facilitate storage) and a second predetermined lowered position (to facilitate deployment) of the setup arm 30.

Figure 8:
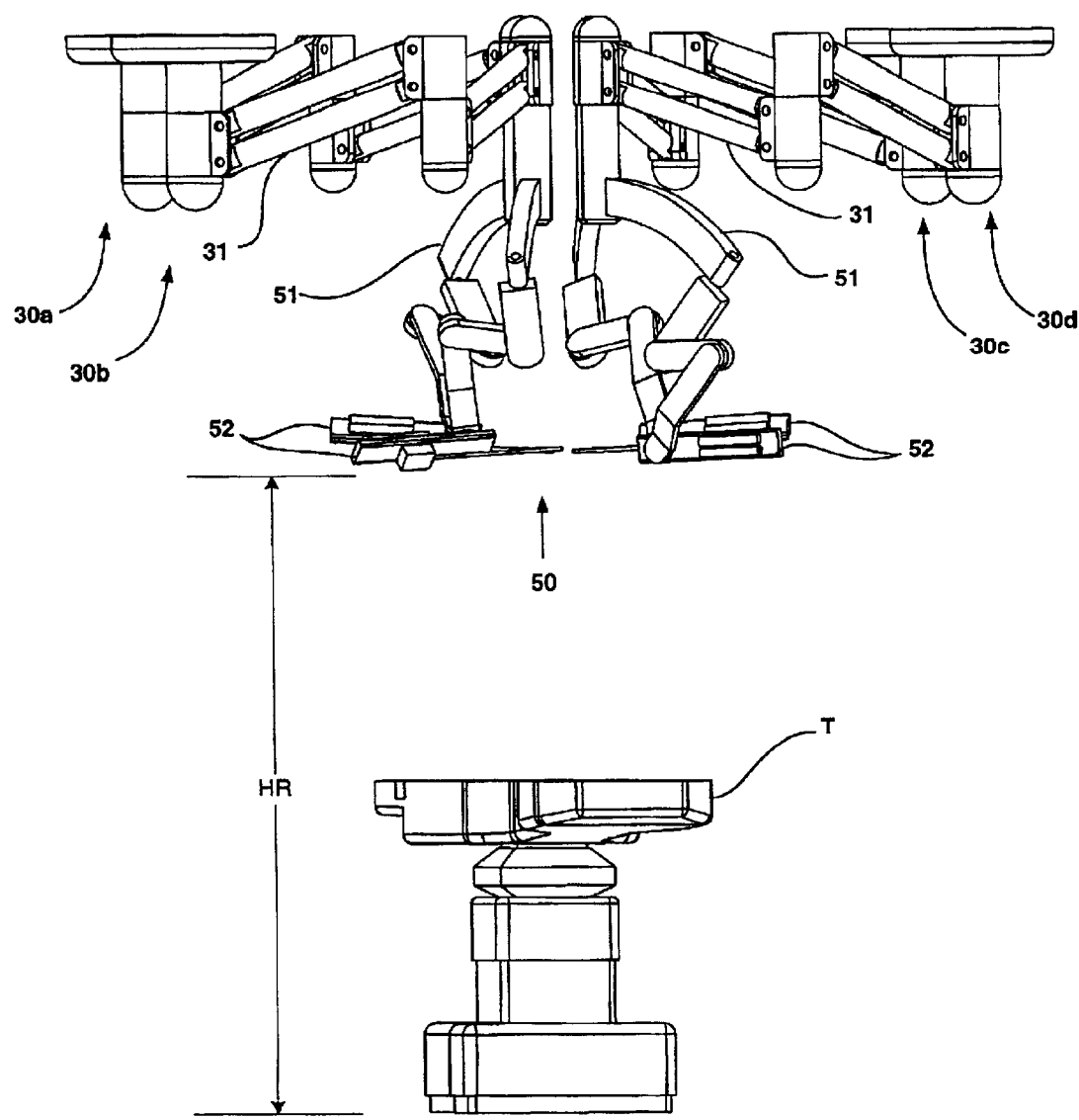
FIG. 8 shows a perspective view of the exemplary ceiling mounted set-up arm system comprising four ceiling mounted set-up arms, shown in the raised, retracted position.

The proximal bracket 34a of upper parallelogram linkage structure 31a is joined by vertical axis pivot joint 37 to a ceiling mounting base or ceiling plate 38, which is in turn fixed to a ceiling-height support structure (not shown). The term "ceiling-height support structure" includes support structures disposed on, adjacent or within an operating room ceiling and includes support structures disposed substantially below an actual ceiling height, especially in the case of a higher-than-typical operating room ceiling. The support structure preferably is sufficiently high above the operating table to permit the arms 30 (and mounted manipulators) to be retracted above personnel standing head level when not in use, as shown in FIG. 8.

The support structure may include existing architectural elements, such as original or reinforced structural elements, joists or beams. Alternatively, the support structure may be a separate dedicated supporting structure providing a mounting surface for mounting base or ceiling plate 38, such as a floor-supported gantry frame. In addition, various alternative forms of ceiling and wall mounting brackets may be substituted for mounting plate 38 to suit particular operating room geometry, existing equipment, room layout, building structural members, and ceiling height. The ceiling base or plate 38 may be fixed or adjustably/removably mounted to the support structure by bolts, brackets or other conventional fastener devices, bonding methods or mounting methods.

The upper and lower parallelogram linkage structures 31a, 31b are pivotally connected, distal bracket of one to proximal bracket of the other, by vertical-axis pivot joint 39. The distal bracket 35b of lower parallelogram linkage structure 31b is joined by vertical axis pivot joint 40 to manipulator support mounting frame 41. Mounting frame 41 includes a horizontal-axis joint 42, pivotally connected to manipulator mounting bracket 43. Bracket 43 may be fixed, for example, by bolts or other conventional fasteners or mounting devices, or by a multi-stop mounting, to base 25 of manipulator 8 as shown in FIGS. 3A and 3B.

Although the setup arm is typically manually positioned, one or more of the joints 37, 39, 40, 42 or linkages 31a, 31b may be power operated and may be computer controlled. Each of these joints typically includes brakes to allow the joints to be locked in position after the arm 30 is deployed. In another optional aspect, the ceiling mounting plate 38 may be mounted by slides or rollers to a lockable ceiling track system (not shown) to permit horizontal repositioning, in one or two dimensions, of the plate 38 and the setup arm 30 to suit particular operational requirements.

Note, that in the exemplary setup arms 30 shown in FIGS. 5 and 6, the manipulator support frame 41, joint 42 and bracket 43 are suited to the geometry of the manipulator shown in FIGS. 3A and 3B. However, a wide range of alternative support frames may be substituted by one of ordinary skill in the art to suit the functional geometry of various existing telesurgical manipulators or future manipulators having different structural arrangements and different numbers of degrees of freedom, including without limitation alternative remote center manipulators, natural center manipulators, computed center manipulators, and manipulators employing a combination of these functional principles.

Figure 7:
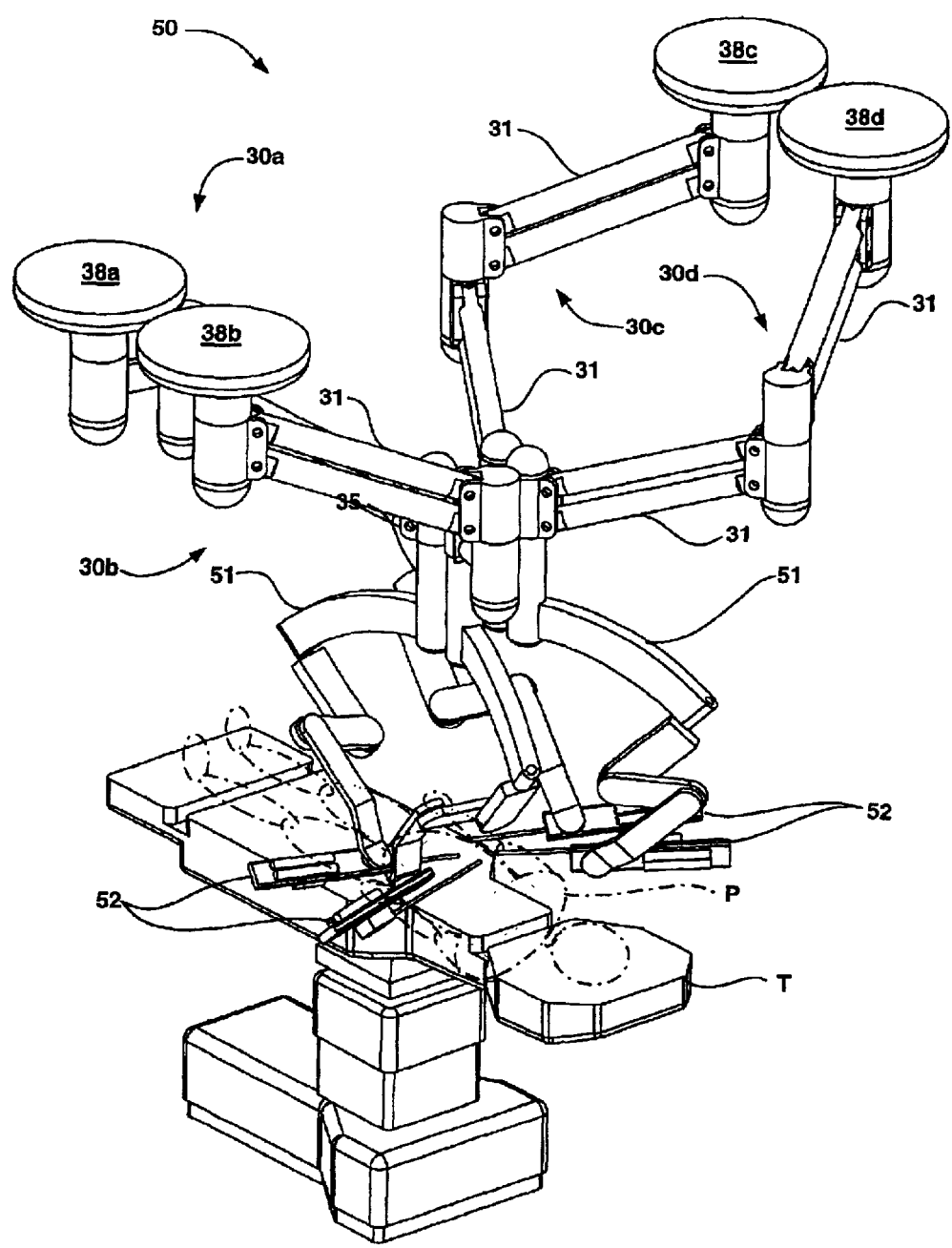
FIG. 7 shows a perspective view of an exemplary patient-side surgical system comprising four ceiling mounted set-up arms having aspects of the invention mounted to the ceiling in two side-by-side pairs on opposite sides of the operating table, shown in the lowered, deployed position.

FIGS. 7 and 8 illustrate an exemplary operating room installation of a patient-side telesurgical system 50 including robotic arm assemblies comprising four ceiling mounted set-up arms 30 a, b, c and d mounted to the ceiling by mounting plates 38 in two side-by-side pairs on opposite sides of the operating table T. FIG. 7 shows a perspective view of such a system, shown with the setup arms 30 in the lowered, deployed position. The balancing mechanisms (36 in FIGS. 5 and 6) are omitted for clarity in FIGS. 7 and 8. Each parallelogram structure 31 is deformed in shear to cause the respective distal brackets 35 to project downward towards patient P resting on table T. In this example, typical of a thoracic procedure, the manipulator support frames 51 have been positioned generally over the patient's chest, hanging below the parallelogram structures 31, permitting the manipulators 52 to be aligned for insertion in both right and left sides of the thorax. Note that assistants will have generally unencumbered access to the sides of table T, the parallelograms 31 being largely positioned above head level.

Note that in this example, the ceiling mounted manipulators 52 are of an alternative design relative to the manipulator 8 of FIGS. 2 and 3, and includes an arc-shaped lateral member mounted to frame 51. As noted above, the manipulator 8 of FIGS. 2, 3A, and 3B, as well as a variety of alternative manipulators, may be mounted to setup arms 30 in generally similar alternative four-arm, ceiling-mounted, patient side systems. Different numbers of setup arms 30 (greater or less than four) may be included in a patient side system and the locations of mounting plates 38 on the ceiling may be selected differently than shown, to suit surgical needs.

The surgical system shown may also include floor/pedestal mounted setup arms as described further below with respect to FIGS. 9 and 10. For purposes of illustration, FIG. 7 shows schematically two manipulators 80 positioned at the sides of table T, e.g., as they may be positioned by the floor mounted setup arms 61 shown in FIG. 10.

FIG. 8 shows a perspective view of the exemplary ceiling mounted set-up arm system 50 of FIG. 7, shown with the setup arms 30 in the raised, retracted position. Each parallelogram structure 31 is deformed in shear to extend upwards toward the ceiling, thus raising the manipulator frame 51 and manipulators 52 above the head level of the assistants.

Figure 9:
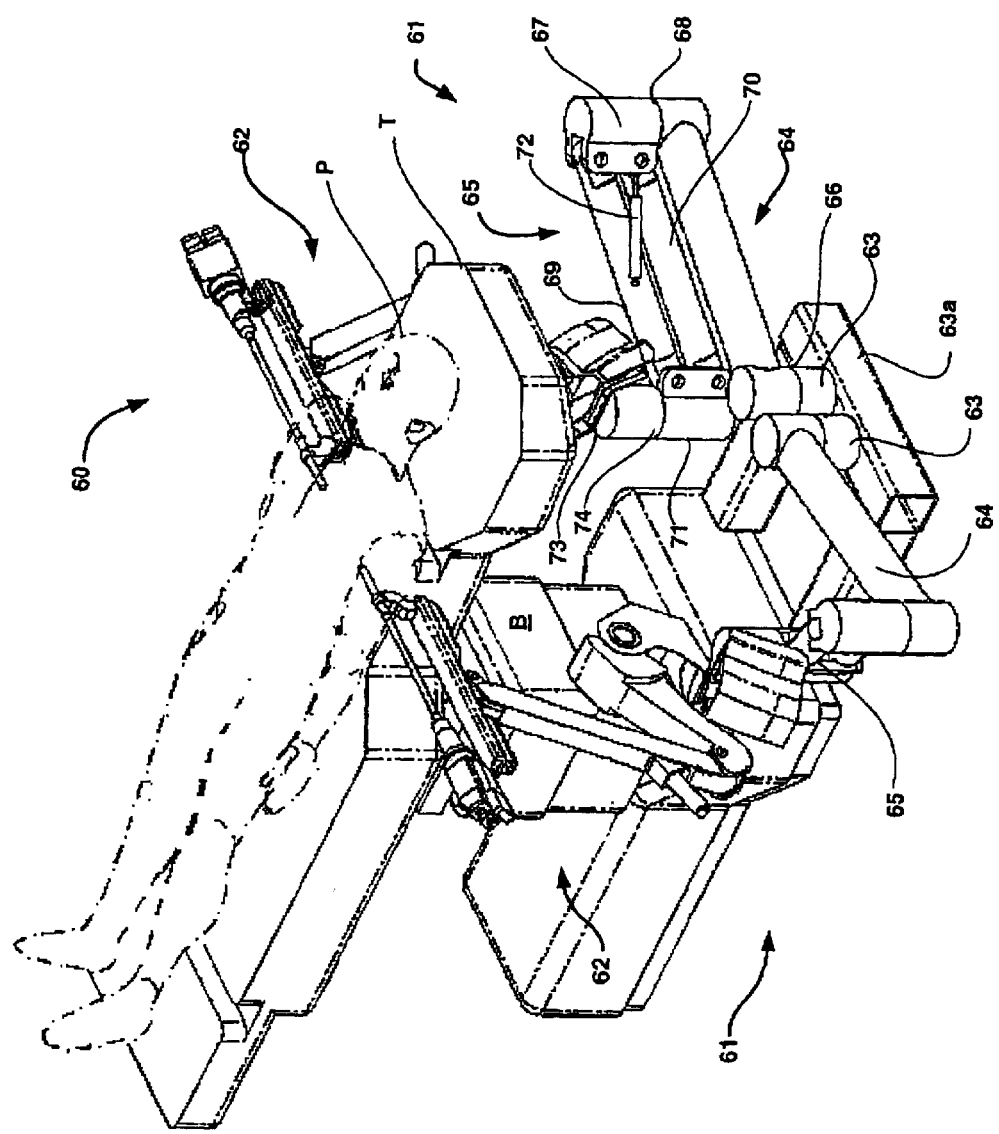
FIGS. 9 and 10 illustrate the an exemplary floor/pedestal mounted setup arm system having aspects of the invention comprising two ECM setup arms, shown deployed at an intermediate height adjacent a thoracic surgical site (FIG. 9) and shown elevated adjacent an abdominal surgical site (FIG. 10)
Figure 10:
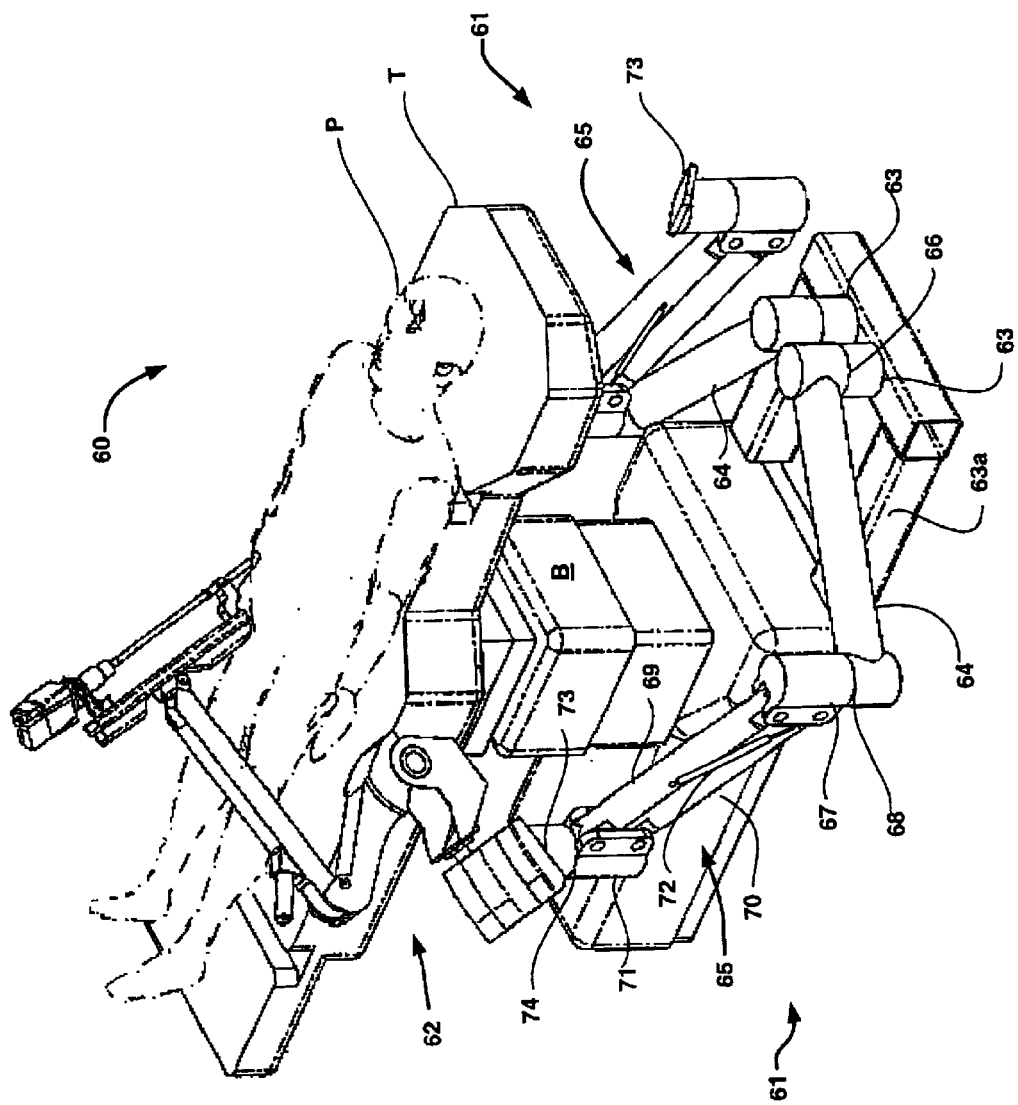

FIGS. 9 and 10 illustrate the an exemplary patient side system 60 including robotic arm assemblies comprising two floor/pedestal mounted setup arms 61 having aspects of the invention. FIG. 9 shows two setup arms 61 deployed at an intermediate height supporting manipulator 62 in a generally horizontal alignment adjacent a thoracic surgical site of patient P lying on operating table T. FIG. 10 shows one setup arm 61 deployed at an elevated height supporting manipulator 62 in an inclined alignment adjacent an abdominal surgical site of patient P. FIG. 10 also shows a second arm 61 in a retracted configuration, (manipulator demounted) stowed below table T.

Each setup arm 61 comprises a mounting base 63 fixed to a support structure extending generally below the table T. In this example, the base 63 is fixed to a dedicated support structure 63a fixed to floor underneath the operating table. Alternatively, the support structure may comprise the table pedestal structure B of table T to which base 63 is mounted, or base 63 may be mounted directly to the floor as a support structure.

This mounting location permits the setup arm 61 to be retracted largely or entirely under the table T when not in use. In the example shown, setup arm 61 includes a lower SCARA-style link 64 (Selective Compliance Articulated Robot Arm) pivoted to base 63 and pivoted to an upper parallelogram linkage structure 65, which in turn supports manipulator 62.

The lower SCARA type link 64 is structurally and functionally generally similar to the individual SCARA-style links of setup arm 7 and 9 shown in FIG. 2. The SCARA-style link 64 is pivotally mounted at its proximal end to base 63 by vertical axis pivot joint 66. The SCARA-style link 64 is pivotally mounted at its distal end to the proximal bracket 67 of parallelogram 65 by vertical axis pivot joint 68. The SCARA link 64 and the pivot 65 provide a broad range of horizontal motion, while being inherently balanced in that the axes of joints 66 and 68 are vertical and the applied gravitational loads are resisted by the SCARA link 64 as a cantilevered member.

The upper parallelogram linkage structure 65 is structurally and functionally generally similar to the individual parallelogram linkage structure 31 of setup arm 30 shown in FIGS. 5 and 6. The parallelogram 65 comprises a proximal bracket 67 pivotally mounting an upper link 69 and a lower link 70, each of which pivot to distal bracket 71 to form a vertically-oriented planar parallelogram configuration which permits vertical motion of distal bracket 71. As in the parallelogram the linkage 31 of FIGS. 5 and 6, the parallelogram 65 is balanced by one or more balance mechanisms 72, such as the diagonally mounted gas springs shown in this example. Distal bracket 71 is joined to manipulator support member 73 via vertical axis pivot 74.

The pivot joints 66, 68 and 74 and parallelogram linkage 65 are manually positionable and lockable in the manner of the joints of setup arm 30 shown in FIGS. 5 and 6, and may likewise optionally be power operated and computer controlled. In the examples shown, the manipulator 62 is an ECM, other manipulators may be mounted and deployed by setup arm 61, such as PSM 8 shown in FIGS. 2 and 3 and the alternative manipulators described with respect to ceiling mount arm 30 of FIGS. 5 and 6.

Figure 11A:
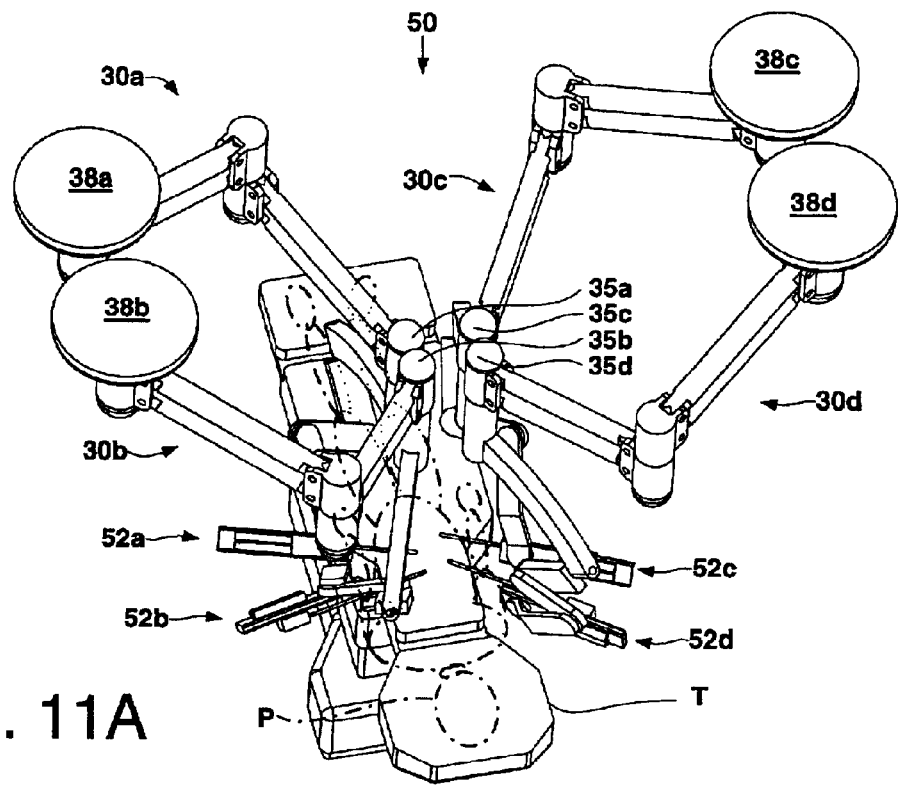
FIGS. 11A through 11C illustrate the range of operational motion of the ceiling mounted setup arms having aspects of the invention, such as those shown in of the surgical system of FIGS. 7 and 8, shown in deployed positions adjacent four different areas of the patient's body.
Figure 11B:
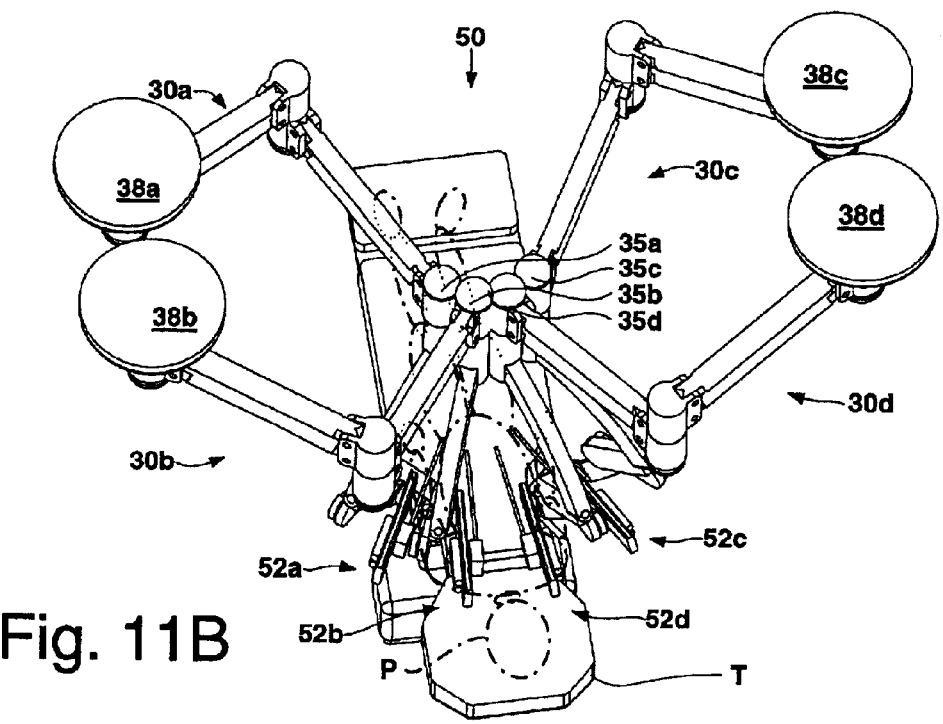
Figure 11C:
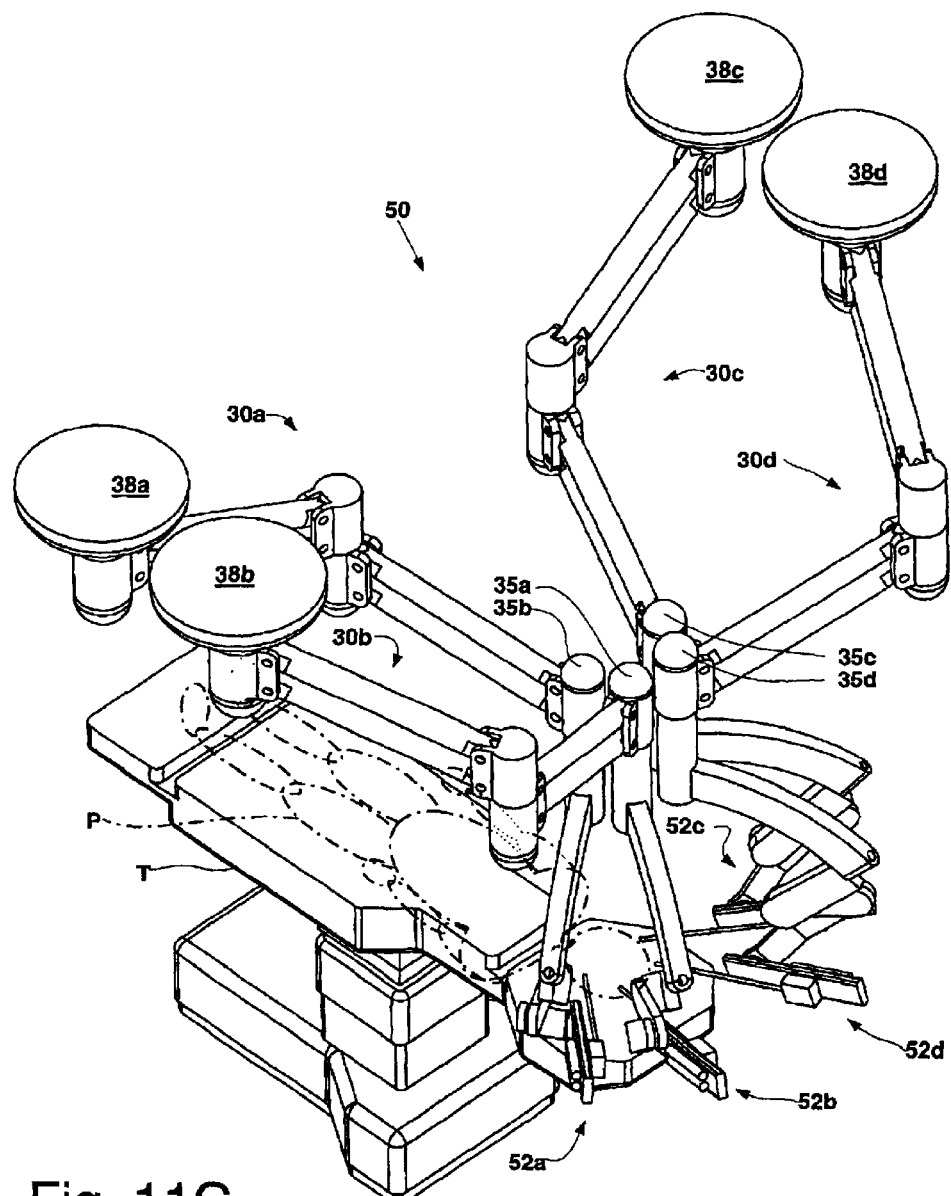

FIGS. 11A through 11C exemplify the range of operational motion of a surgical patient-side system 50, such as that shown in FIGS. 7 and 8, including four of the ceiling mounted setup arms 30a, 30b, 30c and 30d having aspects of the invention. The system 50 is shown in deployed positions adjacent three different areas of the body of patient P lying on operating table T, visualized as seen from above through a transparent ceiling. FIG. 11A illustrates an example of a thoracic or cardiac surgical site deployment; FIG. 11B illustrates an example of an abdominal surgical site deployment; and FIG. 11C illustrates an example of a cranial surgical site deployment. While not shown, it should be appreciated that the system can be deployed to treat a knee surgical site or a foot surgical site, if desired.

In each example, the four ceiling mounting plates 38a, 38b, 38c and 38d are mounted to the ceiling in two side-by-side pairs on opposite sides of the operating table T. The respective setup arms 30a, 30b, 30c and 30d are positioned to bring the resective distal linkage brackets 35a, 35b, 35c and 35d to a position generally above the surgical site, the respective manipulators 52a, 52b, 52c and 52d then being aligned at selected insertion sites adjacent the intended surgical site.

Note that the joints of arms 30a–d have sufficient range of adjustment to be positioned and angled so that the arms approach the vicinity of the surgical site in an generally radial overall pattern, permitting an unencumbered choice of insertion sites and angles, and minimizing space conflicts or "collisions" between adjacent arms or manipulators. A comparison of FIGS. 11A to 11C shows that this generally radial pattern may be maintained for surgical sites throughout the length of the body of patient P.

Figure 12B:
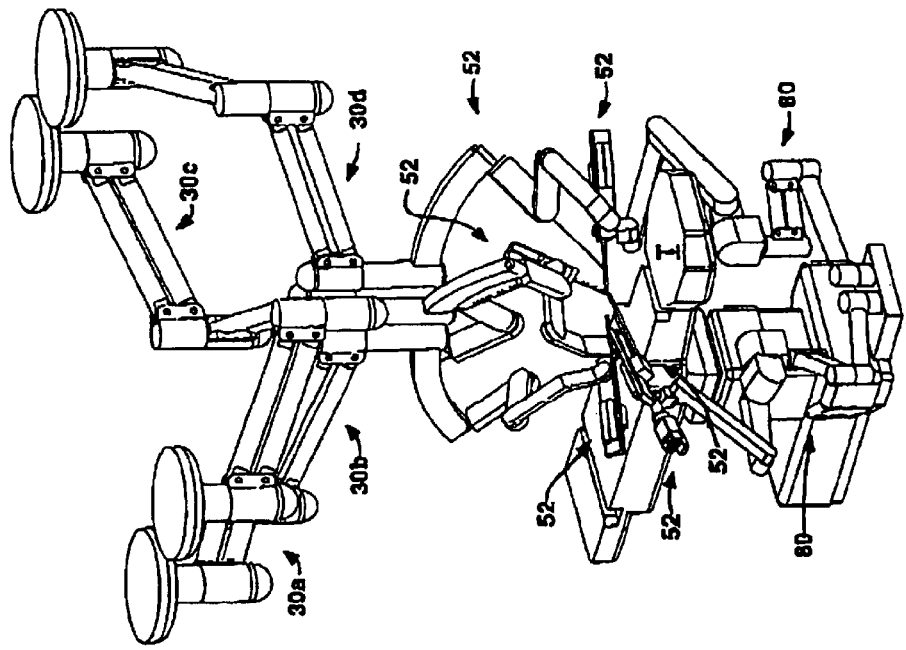
FIGS. 12A and 12B illustrate a comparison contrasting the operating room configurations of (in FIG. 12A) a dual telesurgical arrangement comprising two oppositely positioned cart-mounted patient-side systems such as that shown in FIGS. 1 and 2; and (in FIG. 12B) an exemplary dual telesurgical arrangement of the current invention comprising four ceiling mounted PSM setup arms and two floor mounted arms having aspects of the invention.
Figure 12A:
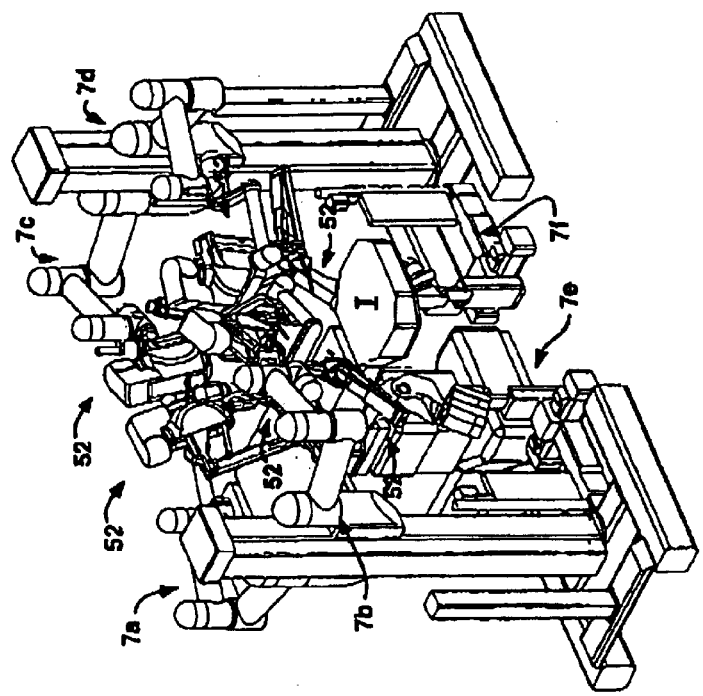

FIGS. 12A and 12B illustrate the improvement in operating room configuration permitted by the ceiling mounted set up arms 30 of the invention relative to exemplary cart mounted setup arms, in the case of a dual surgical system deployed for thoracic surgery, as seen in perspective elevation view from the head of the operating table T. In each case the systems comprise six robotic arms in which six exemplary manipulators 52 (PSM and ECM) are positioned in generally the same insertion sites as in FIG. 11A. Thus, FIGS. 12A and 12B contrast the relative space demands of the alternative setup arms, independent of the manipulator configuration.

FIG. 12A shows a dual telesurgical arrangement comprising two sets of cart-mounted dual PSM setup arms, generally similar to those of patient-side systems 6a and 6b shown in FIGS. 1 and 2, positioned on opposite sides of table T. Note that the arms extend in a spaced-apart pattern across the area adjacent to table T at about the chest and head level of the assistants, and thus restrict movement of the assistants along the table sides. The arrangement can also include two arm carts 7e, 7f, each of which include an additional robotic arm. The arm carts are further described in U.S. patent application Ser. No. 09/433,120, filed Nov. 3, 1999 and U.S. patent application Ser. No. 09/972,322, filed Oct. 5, 2001, the complete disclosures of which are incorporated by reference.

FIG. 12B shows an exemplary dual telesurgical arrangement comprising four ceiling mounted setup arms 30a, 30b, 30c and 30d and two floor mounted arms 80 having aspects of the invention. Note that the setup arms 30 are located almost entirely above head level and/or above the operating table, and thus do not impede the access of the assistants to the table side arm Note that FIG. 12B shows two floor mounted manipulators 80 (see FIG. 10), but in alternative embodiments, manipulators may be positioned along the sides of table T.

As illustrated by the examples of FIGS. 7 to 12B, a multi-arm robotic surgical system may comprise a plurality of robotic surgical manipulators supported by a plurality of setup arms, e.g., being selected from ceiling and floor mounted setup arms having aspects of the invention, such as the ceiling mounted embodiment 30 and the floor mounted setup arm 61. Such multi-arm robotic surgical system are particularly suited to a dual surgeon system in which two or more arms are controlled by the inputs of each of two surgeons, participating cooperatively in the course of surgery. Alternatively, a single surgeon may control three or more PSM type manipulators in addition to a ECM manipulator, e.g., ECM manipulator, e.g., by a method of switching a master input controller from one slave manipulator to another during surgery. Apparatus and methods for such cooperative telesurgical techniques are further described in the above referenced International Application published as WO00/30548 on Jun. 2, 2000;

As illustrated in FIGS. 7 and 12B, an example of a cooperative telesurgical system having aspects of the invention may comprise an ensemble of setup arms including four ceiling mounted arms 30 supporting PSM manipulators and two floor mounted setup arms supporting ECM manipulators(see also FIGS. 9 and 10). The combined use of ceiling and floor mounted setup arms permits a great deal of robotic surgical functionality to be concentrated in the operating room, while still conserving sufficient personnel-usable space adjacent the operating table for effective support by surgical assistants and anesthesiologist. Such as system may enable technically complex and lengthy surgical procedures, such as multiple-vessel coronary artery bypass grafts, to be performed by minimally invasive techniques.

It should be understood that various modifications within the scope of this invention can be made by one of ordinary skill in the art without departing from the spirit thereof. It is therefore wished that this invention to be defined by the scope of the appended claims as broadly as the prior art will permit, and in view of the specification if need be. Accordingly, the scope of the present invention is limited solely by the appended claims.

What is claimed is:

1. A robotic surgery system for performing a surgical procedure on a patient lying on an operating table within an operating room, the room having a ceiling-height support structure extending generally above the table and personnel-usable space adjacent the table, the system comprising:

a mounting base;

a surgical end effector; and a linkage movably supporting the end effector relative to the mounting base, the linkage comprising:

a plurality of driven joints coupled to a servomechanism for moving the end effector so as to manipulate tissues;

at least one pre-configuration link; and a plurality of releasably fixable joints coupled to the at least one pre-configuration link for pre-configuring the linkage, the releasably fixable joints accommodating vertical movement of the end effector relative to the mounting base; and the mounting base is mountable upon the ceiling-height support structure so as to permit the linkage to be pre-configured to extend generally downward from the mounting base to support the end effector adjacent the patient.

2. The robotic surgery system of claim 1, wherein the linkage is pre-configurable to support the end effector adjacent the patient so that the at least one pre-configuration link and the plurality of releasably fixable joints of the pre-configured linkage are disposed generally clear of the personnel-usable space adjacent the operating table.

3. The robotic surgery system of claim 1, further comprising:

a brake system coupled to the fixable joints, the brake system releasably inhibiting inadvertent articulation of the fixable joints previously configured in an at least substantially fixed configuration;

wherein the brake system is biased toward the fixed configuration and the brake system comprises a brake release actuator for releasing the fixable joints to a manually repositionable configuration in which the fixable joints can be manually articulated.

4. The robotic surgery system of claim 3, wherein the fixable joints in the repositionable configuration articulate to accommodate manual translation of the end effector in three dimensions.

5. The robotic surgery system of claim 4, wherein the fixable joints in the repositionable configuration further articulate to accommodate manual rotation of the end effector about least one axis relative to the base.

6. The robotic surgery system of claim 5, wherein the linkage comprises a plurality of fixable links and a plurality of rigid driven links, the fixable links coupled together by the fixable joints, the driven links coupled together by the driven joints, wherein the fixable links are supported by the mounting base and the driven links are supported by the fixable links.

7. The robotic surgery system of claim 6, wherein the fixable links include at least one balanced, fixable, jointed-parallelogram linkage structure extending between a pair of adjacent fixable rotational joints, the jointed-parallelogram structure accommodating motion in a generally vertical direction, and the adjacent rotational joints accommodating pivotal motion about vertical axes.

8. The robotic surgery system of claim 1, wherein the robotic linkage includes a rigid shaft coupled to the end effector, and at least one of the robotic linkage, the servomechanism and a combination of the linkage and servomechanism acts to constrain the shaft to rotation about a pivot point along the shaft, and wherein actuation of the fixable joints moves the pivot point and the shaft.

9. The robotic surgery system of claim 1, the linkage further comprising a joint sensor system coupling the fixable joints to the servomechanism, the sensor system generating joint configuration signals, wherein the servomechanism includes a computer and wherein the joint sensor system transmits the joint configuration signals to the computer.

10. The robotic surgery system of claim 9, wherein the computer calculates a coordinate system transformation between a reference coordinate system affixed relative to the base and the end effector using the joint configuration signals.

11. The robotic surgery system of claim 10, further comprising a plurality of robotic linkages, each linkage including a plurality of joints coupled to the sensor system and supporting an associated end effector, wherein the computer calculates coordinate system transformations between the reference coordinate system and each of the end effectors using the joint configuration signals.

12. The robotic surgery system of claim 11, wherein a joint signal of at least one of the sensors of the sensor system varies with an absolute position of the joint.

13. A support apparatus for supporting a first robotic surgical manipulator relative to a second robotic surgical manipulator, each surgical manipulator coupled to a servomechanism so as to robotically manipulate tissues of a patient body with a surgical end effector while the patient lies on an operating table within an operating room, the room having a ceiling-height support structure extending generally above the table and personnel-usable space adjacent the table, the support apparatus comprising:

a mounting base;

a first support linkage mounted to the base and movably supporting the first manipulator relative to the base, the first support linkage accommodating vertical movement of the first manipulator relative to the mounting base;

the base is mountable upon the ceiling-height support structure so as to permit the first support linkage to be pre-configured to extend generally downward from the base to support the first manipulator adjacent the patient;

a second support linkage supporting the second manipulator relative to the base; and a sensor system coupling the first and second support linkages to the servomechanism, the sensor system transmitting position signals to the servomechanism, the servomechanism calculating at least one of a position and an orientation of the first manipulator relative to the second manipulator using the signals.

14. The support apparatus of claim 13, wherein the first support linkage is pre-configurable to support the first manipulator adjacent the patient so that the pre-configured linkage is disposed generally clear of the personnel-usable space adjacent the operating table.

15. The support apparatus of claim 13, wherein the first support linkage comprises:

an articulated linkage having a plurality of releasably fixable joints coupling the base to the first manipulator so as to allow manual movement of the first manipulator relative to the base for pre-configuring the linkage, and a brake system releasably inhibiting inadvertent movement of the joints, wherein the sensor system is coupled to the joints so that the position signals comprise joint configuration signals of the joints.

16. The support apparatus of claim 15, wherein the brake system is based toward the fixed configuration and the brake system comprises a brake release actuator for releasing the fixable joints to a manually repositionable configuration in which the fixable joints can be manually articulated.

17. The support apparatus of claim 16, wherein the brake system can release the joints upon actuation of a single actuator.

18. The support apparatus of claim 17, wherein the joints articulate to accommodate manual translation of the manipulator and handle in three dimensions.

19. The support apparatus of claim 18, wherein the joints further articulate to accommodate manual rotation of an end effector coupled to the first manipulator about at least one axis relative to the base.

20. The support apparatus of claim 15, wherein the first support linkage is balanced about the joints.

21. The support apparatus of claim 15, wherein the first support linkage includes at least one balanced, fixable, jointed-parallelogram linkage structure extending between a pair of adjacent fixable rotational joints, the jointed-parallelogram structure accommodating motion in a generally vertical direction, and the adjacent rotational joints accommodating pivotal motion about vertical axes.

22. A method for preparing for robotic surgery on a patient lying on an operating table within an operating room, the room having a ceiling-height support structure extending generally above the table and personnel-usable space adjacent the table, the surgery employing a surgical manipulator having servo-mechanically driven joints, the method comprising:
    maintaining driven joints of the surgical manipulator sufficiently near mid points of travel of the joints so as to inhibit interference with a limit of travel of the manipulator within an intended worksite;
    pre-positioning the manipulator while maintaining the driven joints near the mid points by manually articulating a linkage coupled to the manipulator and to a mounting base, the linkage accommodating vertical movement of the manipulator relative to the mounting base, and the base being mounted upon the ceiling-height support structure so that the pre-positioned linkage extends generally downward from the base to support the manipulator adjacent the patient; and
    restraining the positioned manipulator with a brake system so as to prevent articulation of the linkage.

23. The method of claim 22, wherein the pre-positioning step comprises pre-positioning the linkage so that the pre-positioned linkage is disposed generally clear of the personnel-usable space adjacent the operating table.

24. The method of claim 22, wherein the pre-positioning step comprises orienting a manipulator shaft towards an internal access site, the manipulator being adapted to pivot the shaft about the access site so as to manipulate tissues endoscopically.

25. A robotic surgery system for performing a surgical procedure on a patient lying on an operating table within an operating room, the room having a support structure extending generally below the table and personnel-usable space adjacent the table, the system comprising:
    a base;
    a surgical end effector; and
    a linkage movably supporting the end effector relative to the base, the linkage comprising:
    a plurality of driven joints coupled to a servomechanism for moving the end effector so as to manipulate tissues;
    at least one pre-configuration link; and
    a plurality of releasably fixable joints coupled to the at least one pre-configuration link for pre-configuring the linkage, the releasably fixable joints accommodating vertical movement of the end effector relative to the base; and the base is mountable upon the support structure below the operating table so as to permit the linkage to be pre-configured to extend generally upward from the base to support the end effector adjacent the patient.

26. The robotic surgery system of claim 25, wherein the linkage is pre-configurable to support the end effector adjacent the patient so that the at least one pre-configuration link and the plurality of releasably fixable joints of the pre-configured linkage are disposed generally clear of the personnel-usable space adjacent the operating table.

27. The robotic surgery system of claim 25, further comprising:
    a brake system coupled to the fixable joints, the brake system releasably inhibiting inadvertent articulation of the fixable joints previously configured in an at least substantially fixed configuration;
    wherein the brake system is biased toward the fixed configuration and the brake system comprises a brake release actuator for releasing the fixable joints to a manually repositionable configuration in which the fixable joints can be manually articulated.

28. The robotic surgery system of claim 27, wherein the fixable joints in the repositionable configuration articulate to accommodate manual translation of the end effector in three dimensions.

29. The robotic surgery system of claim 28, wherein the fixable joints in the repositionable configuration further articulate to accommodate manual rotation of the end effector about least one axis relative to the base.

30. The robotic surgery system of claim 29, wherein the linkage comprises a plurality of fixable links and a plurality of rigid driven links, the fixable links coupled together by the fixable joints, the driven links coupled together by the driven joints, wherein the fixable links are supported by the mounting base and the driven links are supported by the fixable links.

31. The robotic surgery system of claim 30, wherein the fixable links include at least one balanced, fixable, jointed-parallelogram linkage structure extending between a pair of adjacent fixable rotational joints, the jointed-parallelogram structure accommodating motion in a generally vertical direction, and the adjacent rotational joints accommodating pivotal motion about vertical axes.

32. The robotic surgery system of claim 25, wherein the robotic linkage includes a rigid shaft coupled to the end effector, and at least one of the robotic linkage, the servomechanism and a combination of the linkage and servomechanism acts to constrain the shaft to rotation about a pivot point along the shaft, and wherein actuation of the fixable joints moves the pivot point and the shaft.

33. The robotic surgery system of claim 25, the linkage further comprising a joint sensor system coupling the fixable joints to the servomechanism, the sensor system generating joint configuration signals, wherein the servomechanism includes a computer and wherein the joint sensor system transmits the joint configuration signals to the computer.

34. The robotic surgery system of claim 33, wherein the computer calculates a coordinate system transformation between a reference coordinate system affixed relative to the base and the end effector using the joint configuration signals.

35. The robotic surgery system of claim 34, further comprising a plurality of robotic linkages, each linkage including a plurality of joints coupled to the sensor system and supporting an associated end effector, wherein the computer calculates coordinate system transformations between the reference coordinate system and each of the end effectors using the joint configuration signals.

36. The robotic surgery system of claim 35, wherein a joint signal of at least one of the sensors of the sensor system varies with an absolute position of the joint.

37. A support apparatus for supporting a first robotic surgical manipulator relative to a second robotic surgical manipulator, each surgical manipulator coupled to a servomechanism so as to robotically manipulate tissues of a patient body with a surgical end effector while the patient lies on an operating table within an operating room, the room having a support structure extending generally below the table and personnel-usable space adjacent the table, the support apparatus comprising:

a base;

a first support linkage mounted to the base and movably supporting the first manipulator relative to the base, the first support linkage accommodating vertical movement of the first manipulator relative to the base;

the base is mountable upon the support structure below the operating table so as to permit the first support linkage to be pre-configured to extend generally upward from the base to support the first manipulator adjacent the patient;

a second support linkage supporting the second manipulator relative to the base; and a sensor system coupling the first and second support linkages to the servomechanism, the sensor system transmitting position signals to the servomechanism, the servomechanism calculating at least one of a position and an orientation of the first manipulator relative to the second manipulator using the signals.

38. The support apparatus of claim 37, wherein the first support linkage is pre-configurable to support the first manipulator adjacent the patient so that the pre-configured linkage is disposed generally clear of the personnel-usable space adjacent the operating table.

39. The support apparatus of claim 37, wherein the first support linkage comprises:

an articulated linkage having a plurality of releasably fixable joints coupling the base to the first manipulator so as to allow manual movement of the first manipulator relative to the base for pre-configuring the linkage, and a brake system releasably inhibiting inadvertent movement of the joints, wherein the sensor system is coupled to the joints so that the position signals comprise joint configuration signals of the joints.

40. The support apparatus of claim 39, wherein the brake system is biased toward the fixed configuration and the brake system comprises a brake release actuator for releasing the fixable joints to a manually repositionable configuration in which the fixable joints can be manually articulated.

41. The support apparatus of claim 40, wherein the brake system can release the joints upon actuation of a single actuator.

42. The support apparatus of claim 41, wherein the joints articulate to accommodate manual translation of the manipulator and handle in three dimensions.

43. The support apparatus of claim 42, wherein the joints further articulate to accommodate manual rotation of an end effector coupled to the first manipulator about at least one axis relative to the base.

44. The support apparatus of claim 39, wherein the first support linkage is balanced about the joints.

45. The support apparatus of claim 39, wherein the first support linkage includes at least one balanced, fixable, jointed-parallelogram linkage structure extending between a pair of adjacent fixable rotational joints, the jointed-parallelogram structure accommodating motion in a generally vertical direction, and the adjacent rotational joints accommodating pivotal motion about vertical axes.

46. A method for preparing for robotic surgery on a patient lying on an operating table within an operating room, the room having a support structure extending generally below the table and personnel-usable space adjacent the table, the surgery employing a surgical manipulator having servomechanically driven joints, the method comprising:

maintaining driven joints of the surgical manipulator sufficiently near mid points of travel of the joints so as to inhibit interference with a limit of travel of the manipulator within an intended worksite;

pre-positioning the manipulator while maintaining the driven joints near the mid points by manually articulating a linkage coupled to the manipulator and to a mounting base, the linkage accommodating vertical movement of the manipulator relative to the mounting base, and the base being mounted upon the support structure below the operating table so that the pre-positioned positioned linkage to extends generally upward from the base to support the manipulator adjacent the patient; and restraining the positioned manipulator with a brake system so as to prevent articulation of the linkage.

47. A robotic surgery system for performing a surgical procedure on a patient lying on an operating table within an operating room, the room having personnel-usable space adjacent the table, having a ceiling-height support structure extending generally above the table and having a below-table support structure extending generally below the table, the system comprising:

at least one ceiling-height-mounted robotic arm assembly comprising:

a first base;

a first surgical manipulator coupled to an first end effector;

a first linkage including a plurality of releasably fixable joints for pre-configuring the first linkage, the releasably fixable joints accommodating vertical movement of the first manipulator relative to the first base; and the first base is mountable upon the ceiling-height support structure so as to permit the first linkage to be pre-configured to extend generally downward from the first base to support the first end effector adjacent the patient; and at least one below-table-mounted robotic arm assembly comprising:

a second base;

a second surgical manipulator coupled to an second end effector;

a second linkage including a plurality of releasably fixable joints for pre-configuring the second linkage, the releasably fixable joints accommodating vertical movement of the second manipulator relative to the second base; and the second base is mountable upon the below table support structure so as to permit the second linkage to be pre-configured to extend generally upward from the second base to support the second end effector adjacent the patient.

48. The robotic surgery system of claim 47, wherein the first and second linkages are pre-configurable to support the first and second end effectors adjacent the patient so that the at least one ceiling-height-mounted robotic arm assembly and the at least one below-table-mounted robotic arm assembly are disposed generally clear of the personnel-usable space adjacent the operating table.

49. The robotic surgery system of claim 48, wherein at least one of the ceiling-height-mounted robotic arm assembly and the below-table-mounted robotic arm assembly further comprises:

brake system coupled to the fixable joints, the brake system releasably inhibiting inadvertent articulation of the fixable joints previously configured in an at least substantially fixed configuration;

wherein the brake system is biased toward the fixed configuration and the brake system comprises a brake release actuator for releasing the fixable joints to a manually repositionable configuration in which the fixable joints can be manually articulated.

50. The robotic surgery system of claim 49, wherein the at least one ceiling-height-mounted robotic arm assembly and the at least one below-table-mounted robotic arm assembly include:

at least a total of four robotic arm assemblies operatively controllable by a single operator, wherein at least one of the manipulator-supported end effectors is an endoscopic image capture device.

51. The robotic surgery system of claim 49, wherein the at least one ceiling-height-mounted robotic arm assembly and the at least one below-table-mounted robotic arm assembly include:

at least four robotic arm assemblies, wherein at least one of the manipulator-supported end effectors being an endoscopic image capture device, at least one of the robotic arm assemblies being simultaneously operatively controllable by a different operator than at least one of the other robotic arm assemblies.

52. The robotic surgery system of claim 51, wherein the robotic arm assemblies include:

at least three robotic arm assemblies which are operatively controllable by a first operator; and at least three robotic arm assemblies which are simultaneously operatively controllable by a second operator.

53. A robotic surgery system for performing a surgical procedure on a patient lying on an operating table within an operating room, the room having a ceiling-height support structure extending generally above the table and personnel-usable space adjacent the table, the system comprising:

a mounting base;

a surgical end effector; and a linkage movably supporting the end effector relative to the mounting base, the linkage comprising:

a plurality of driven joints coupled to a servomechanism for moving the end effector so as to manipulate tissues;

at least one pre-configuration link;

a plurality of releasably fixable joints coupled to the at least one pre-configuration link for pre-configuring the linkage, the releasably fixable joints accommodating vertical movement of the end effector relative to the mounting base;

the mounting base is mountable upon the ceiling-height support structure so as to permit the linkage to be pre-configured to extend generally downward from the mounting base to support the end effector adjacent the patient; and a brake system coupled to the fixable joints, the brake system releasably inhibiting inadvertent articulation of the fixable joints previously configured in an at least substantially fixed configuration, wherein the brake system is biased toward the fixed configuration and the brake system comprises a brake release actuator for releasing the fixable joints to a manually repositionable configuration in which the fixable joints can be manually articulated.

54. A support apparatus for supporting a first robotic surgical manipulator relative to a second robotic surgical manipulator, each surgical manipulator coupled to a servomechanism so as to robotically manipulate tissues of a patient body with a surgical end effector while the patient lies on an operating table within an operating room, the room having a ceiling-height support structure extending generally above the table and personnel-usable space adjacent the table, the support apparatus comprising:

a mounting base;

a first support linkage mounted to the base and movably supporting the first manipulator relative to the base, the first support linkage accommodating vertical movement of the first manipulator relative to the mounting base;

the base is mountable upon the ceiling-height support structure so as to permit the first support linkage to be pre-configured to extend generally downward from the base to support the first manipulator adjacent the patient;

a second support linkage supporting the second manipulator relative to the base; and a sensor system coupling the first and second support linkages to the servomechanism, the sensor system transmitting position signals to the servomechanism, the servomechanism calculating at least one of a position and an orientation of the first manipulator relative to the second manipulator using the signals;

wherein the first support linkage comprises an articulated linkage having a plurality of releasably fixable joints coupling the base to the first manipulator so as to allow manual movement of the first manipulator relative to the base for pre-configuring the linkage, and a brake system releasably inhibiting inadvertent movement of the joints, wherein the sensor system is coupled to the joints so that the position signals comprise joint configuration signals of the joints, wherein the brake system is biased toward the fixed configuration and the brake system comprises a brake release actuator for releasing the fixable joints to a manually repositionable configuration in which the fixable joints can be manually articulated.

55. A support apparatus for supporting a first robotic surgical manipulator relative to a second robotic surgical manipulator, each surgical manipulator coupled to a servomechanism so as to robotically manipulate tissues of a patient body with a surgical end effector while the patient lies on an operating table within an operating room, the room having a ceiling-height support structure extending generally above the table and personnel-usable space adjacent the table, the support apparatus comprising:

a mounting base;

a first support linkage mounted to the base and movably supporting the first manipulator relative to the base, the first support linkage accommodating vertical movement of the first manipulator relative to the mounting base;

the base is mountable upon the ceiling-height support structure so as to permit the first support linkage to be pre-configured to extend generally downward from the base to support the first manipulator adjacent the patient;

a second support linkage supporting the second manipulator relative to the base; and a sensor system coupling the first and second support linkages to the servomechanism, the sensor system transmitting position signals to the servomechanism, the servomechanism calculating at least one of a position and an orientation of the first manipulator relative to the second manipulator using the signals;

wherein the first support linkage comprises an articulated linkage having a plurality of releasably fixable joints coupling the base to the first manipulator so as to allow manual movement of the first manipulator relative to the base for pre-configuring the linkage, a brake system releasably inhibiting inadvertent movement of the joints, wherein the sensor system is coupled to the joints so that the position signals comprise joint configuration signals of the joints, and at least one balanced, fixable, jointed-parallelogram linkage structure extending between a pair of adjacent fixable rotational joints, the jointed-parallelogram structure accommodating motion in a generally vertical direction, and the adjacent rotational joints accommodating pivotal motion about vertical axes.

56. A robotic surgery system for performing a surgical procedure on a patient lying on an operating table within an operating room, the room having a support structure extending generally below the table and personnel-usable space adjacent the table, the system comprising:

a base;

a surgical end effector; and a linkage movably supporting the end effector relative to the base, the linkage comprising:

a plurality of driven joints coupled to a servomechanism for moving the end effector so as to manipulate tissues;

at least one pre-configuration link;

a plurality of releasably fixable joints coupled to the at least one pre-configuration link for pre-configuring the linkage, the releasably fixable joints accommodating vertical movement of the end effector relative to the base;

the base is mountable upon the support structure so as to permit the linkage to be pre-configured to extend generally upward from the base to support the end effector adjacent the patient; and a brake system coupled to the fixable joints, the brake system releasably inhibiting inadvertent articulation of the fixable joints previously configured in an at least substantially fixed configuration, wherein the brake system is biased toward the fixed configuration and the brake system comprises a brake release actuator for releasing the fixable joints to a manually repositionable configuration in which the fixable joints can be manually articulated.

57. A support apparatus for supporting a first robotic surgical manipulator relative to a second robotic surgical manipulator, each surgical manipulator coupled to a servomechanism so as to robotically manipulate tissues of a patient body with a surgical end effector while the patient lies on an operating table within an operating room, the room having a support structure extending generally below the table and personnel-usable space adjacent the table, the support apparatus comprising:

a base;

a first support linkage mounted to the base and movably supporting the first manipulator relative to the base, the first support linkage accommodating vertical movement of the first manipulator relative to the base;

the base is mountable upon the support structure so as to permit the first support linkage to be pre-configured to extend generally upward from the base to support the first manipulator adjacent the patient;

a second support linkage supporting the second manipulator relative to the base; and a sensor system coupling the first and second support linkages to the servomechanism, the sensor system transmitting position signals to the servomechanism, the servomechanism calculating at least one of a position and an orientation of the first manipulator relative to the second manipulator using the signals;

wherein the first support linkage comprises an articulated linkage having a plurality of releasably fixable joints coupling the base to the first manipulator so as to allow manual movement of the first manipulator relative to the base for pre-configuring the linkage, and a brake system releasably inhibiting inadvertent movement of the joints, wherein the sensor system is coupled to the joints so that the position signals comprise joint configuration signals of the joints, wherein the brake system is biased toward the fixed configuration and the brake system comprises a brake release actuator for releasing the fixable joints to a manually repositionable configuration in which the fixable joints can be manually articulated.

58. A support apparatus for supporting a first robotic surgical manipulator relative to a second robotic surgical manipulator, each surgical manipulator coupled to a servomechanism so as to robotically manipulate tissues of a patient body with a surgical end effector while the patient lies on an operating table within an operating room, the room having a support structure extending generally below the table and personnel-usable space adjacent the table, the support apparatus comprising:

a base;

a first support linkage mounted to the base and movably supporting the first manipulator relative to the base, the first support linkage accommodating vertical movement of the first manipulator relative to the base;

the base is mountable upon the support structure so as to permit the first support linkage to be pre-configured to extend generally upward from the base to support the first manipulator adjacent the patient;

a second support linkage supporting the second manipulator relative to the base; and a sensor system coupling the first and second support linkages to the servomechanism, the sensor system transmitting position signals to the servomechanism, the servomechanism calculating at least one of a position and an orientation of the first manipulator relative to the second manipulator using the signals;

wherein the first support linkage comprises an articulated linkage having a plurality of releasably fixable joints coupling the base to the first manipulator so as to allow manual movement of the first manipulator relative to the base for pre-configuring the linkage, a brake system releasably inhibiting inadvertent movement of the joints, wherein the sensor system is coupled to the joints so that the position signals comprise joint configuration signals of the joints, and at least one balanced, fixable, jointed-parallelogram linkage structure extending between a pair of adjacent fixable rotational joints, the jointed-parallelogram structure accommodating motion in a generally vertical direction, and the adjacent rotational joints accommodating pivotal motion about vertical axes.

59. A robotic surgery system for performing a surgical procedure on a patient lying on an operating table within an operating room, the room having personnel-usable space adjacent the table, having a ceiling-height support structure extending generally above the table and having a below-table support structure extending generally below the table, the system comprising:

at least one ceiling-height-mounted robotic arm assembly comprising:

a first base;

a first surgical manipulator coupled to an first end effector;

a first linkage including a plurality of releasably fixable joints for pre-configuring the first linkage, the releasably fixable joints accommodating vertical movement of the first manipulator relative to the first base; and the first base is mountable upon the ceiling-height support structure so as to permit the first linkage to be pre-configured to extend generally downward from the first base to support the first end effector adjacent the patient; and at least one below-table-mounted robotic arm assembly comprising;

a second base;

a second surgical manipulator coupled to an second end effector;

a second linkage including a plurality of releasably fixable joints for pre-configuring the second linkage, the releasably fixable joints accommodating vertical movement of the second manipulator relative to the second base; and the second base is mountable upon the below table support structure so as to permit the second linkage to be pre-configured to extend generally upward from the second base to support the second end effector adjacent the patient;

wherein the first and second linkages are pre-configurable to support the first and second end effectors adjacent the patient so that the at least one ceiling-height-mounted robotic arm assembly and the at least one below-table-mounted robotic arm assembly are disposed generally clear of the personnel-usable space adjacent the operating table;

wherein at least one of the ceiling-height-mounted robotic arm assembly and the below-table-mounted robotic arm assembly further includes a brake system coupled to the fixable joints, the brake system releasably inhibiting inadvertent articulation of the fixable joints previously configured in an at least substantially fixed configuration, wherein the brake system is biased toward the fixed configuration and the brake system comprises a brake release actuator for releasing the fixable joints to a manually repositionable configuration in which the fixable joints can be manually articulated.

* * * * *